(12) United States Patent
Fitzgibbon et al.

(10) Patent No.: US 11,799,648 B2
(45) Date of Patent: *Oct. 24, 2023

(54) METHOD AND APPARATUS TO FACILITATE TRANSMISSION OF AN ENCRYPTED ROLLING CODE

(71) Applicant: The Chamberlain Group LLC, Oak Brook, IL (US)

(72) Inventors: James J. Fitzgibbon, Batavia, IL (US); Eric Gregori, Lindenhurst, IL (US); Edward Thomas Laird, Lombard, IL (US)

(73) Assignee: The Chamberlain Group LLC, Oak Brook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/194,923

(22) Filed: Mar. 8, 2021

(65) Prior Publication Data

US 2021/0281405 A1    Sep. 9, 2021

Related U.S. Application Data

(63) Continuation of application No. 13/777,787, filed on Feb. 26, 2013, now Pat. No. 10,944,559, which is a continuation of application No. 11/501,455, filed on Aug. 9, 2006, now Pat. No. 8,422,667, which is a continuation-in-part of application No. 11/480,288, filed on Jun. 30, 2006, now Pat. No. 7,561,075, which (Continued)

(51) Int. Cl.
| | |
|---|---|
| *H04L 9/12* | (2006.01) |
| *H04L 9/08* | (2006.01) |
| *H04L 9/32* | (2006.01) |
| *G07C 9/00* | (2020.01) |

(52) U.S. Cl.
CPC .............. *H04L 9/12* (2013.01); *H04L 9/0891* (2013.01); *H04L 9/3226* (2013.01); *G07C 2009/00253* (2013.01); *H04L 2209/80* (2013.01)

(58) Field of Classification Search
None
See application file for complete search history.

(56) References Cited

U.S. PATENT DOCUMENTS

| | | | |
|---|---|---|---|
| 29,525 | A | 8/1860 | Sherman |
| 30,957 | A | 12/1860 | Campbell |

(Continued)

FOREIGN PATENT DOCUMENTS

| | | |
|---|---|---|
| AU | 645228 | 2/1992 |
| AU | 710682 | 11/1996 |

(Continued)

OTHER PUBLICATIONS

'Access Transmitters-Access Security System', pp. 1-2, Dated Jul. 16, 1997. http://www.webercreations.com/access/security.html.

(Continued)

*Primary Examiner* — Benjamin E Lanier
(74) *Attorney, Agent, or Firm* — Barta, Jones & Foley, PLLC

(57) ABSTRACT

An encrypted rolling code, a plurality of differing data bit order patterns, and a plurality of differing data inversion patterns are provided. One then selects a particular one of each of these patterns and uses those selected patterns as transmission characteristics when transmitting at least part of the encrypted rolling code.

21 Claims, 9 Drawing Sheets

Related U.S. Application Data is a continuation of application No. 11/044,411, filed on Jan. 27, 2005, now Pat. No. 7,071,850, said application No. 11/501,455 is a continuation-in-part of application No. 11/172,525, filed on Jun. 30, 2005, now Pat. No. 9,148,409.

(56) References Cited

U.S. PATENT DOCUMENTS

| | | |
|---|---|---|
| 35,364 A | 5/1862 | Cox |
| 2,405,500 A | 8/1946 | Gustav |
| 3,716,865 A | 2/1973 | Willmott |
| 3,735,106 A | 5/1973 | Hollaway |
| 3,792,446 A | 2/1974 | Mcfiggins |
| 3,798,359 A | 3/1974 | Feistel |
| 3,798,360 A | 3/1974 | Feistel |
| 3,798,544 A | 3/1974 | Norman |
| 3,798,605 A | 3/1974 | Feistel |
| 3,845,277 A | 10/1974 | Spetz |
| 3,890,601 A | 6/1975 | Pietrolewicz |
| 3,906,348 A | 9/1975 | Willmott |
| 3,938,091 A | 2/1976 | Atalla |
| 4,037,201 A | 7/1977 | Willmott |
| 4,064,404 A | 12/1977 | Willmott |
| RE29,525 E | 1/1978 | Willmott |
| 4,078,152 A | 3/1978 | Tuckerman |
| 4,097,859 A | 6/1978 | Looschen |
| 4,138,735 A | 2/1979 | Allocca |
| 4,178,549 A | 12/1979 | Ledenbach |
| 4,195,196 A | 3/1980 | Feistel |
| 4,195,200 A | 3/1980 | Feistel |
| 4,196,310 A | 4/1980 | Forman |
| 4,218,738 A | 8/1980 | Matyas |
| 4,243,976 A | 1/1981 | Warner |
| 4,255,742 A | 3/1981 | Gable |
| 4,304,962 A | 12/1981 | Fracassi |
| 4,305,060 A | 12/1981 | Apple |
| 4,316,055 A | 2/1982 | Feistel |
| 4,326,098 A | 4/1982 | Bouricius |
| 4,327,444 A | 4/1982 | Court |
| 4,328,414 A | 5/1982 | Atalla |
| 4,328,540 A | 5/1982 | Matsuoka |
| RE30,957 E | 6/1982 | Feistel |
| 4,380,762 A | 4/1983 | Capasso |
| 4,385,296 A | 5/1983 | Tsubaki |
| 4,387,455 A | 6/1983 | Schwartz |
| 4,387,460 A | 6/1983 | Boutmy |
| 4,393,269 A | 7/1983 | Konheim |
| 4,418,333 A | 11/1983 | Schwarzbach |
| 4,426,637 A | 1/1984 | Apple |
| 4,445,712 A | 5/1984 | Smagala-Romanoff |
| 4,447,890 A | 5/1984 | Duwel |
| 4,454,509 A | 6/1984 | Buennagel |
| 4,464,651 A | 8/1984 | Duhame |
| 4,468,787 A | 8/1984 | Keiper |
| 4,471,493 A | 9/1984 | Schober |
| 4,471,593 A | 9/1984 | Ragland |
| 4,491,774 A | 1/1985 | Schmitz |
| 4,509,093 A | 4/1985 | Stellberger |
| 4,529,980 A | 7/1985 | Liotine |
| 4,535,333 A | 8/1985 | Twardowski |
| 4,566,044 A | 1/1986 | Langdon |
| 4,574,247 A | 3/1986 | Jacob |
| 4,578,530 A | 3/1986 | Zeidler |
| 4,580,111 A | 4/1986 | Swanson |
| 4,581,606 A | 4/1986 | Mallory |
| 4,590,470 A | 5/1986 | Koenig |
| 4,593,155 A | 6/1986 | Hawkins |
| 4,596,898 A | 6/1986 | Pemmaraju |
| 4,596,985 A | 6/1986 | Bongard |
| 4,599,489 A | 7/1986 | Cargile |
| 4,602,357 A | 7/1986 | Yang |
| 4,611,198 A | 9/1986 | Levinson |
| 4,623,887 A | 11/1986 | Welles |
| 4,626,848 A | 12/1986 | Ehlers |
| 4,628,315 A | 12/1986 | Douglas |
| 4,630,035 A | 12/1986 | Stahl |
| 4,633,247 A | 12/1986 | Hegeler |
| 4,638,433 A | 1/1987 | Schindler |
| 4,646,080 A | 2/1987 | Genest |
| 4,652,860 A | 3/1987 | Weishaupt |
| 4,653,076 A | 3/1987 | Jerrim |
| 4,670,746 A | 6/1987 | Taniguchi |
| 4,677,284 A | 6/1987 | Genest |
| 4,686,529 A | 8/1987 | Kleefeldt |
| 4,695,839 A | 9/1987 | Barbu |
| 4,703,359 A | 10/1987 | Rumbolt |
| 4,710,613 A | 12/1987 | Shigenaga |
| 4,716,301 A | 12/1987 | Willmott |
| 4,720,860 A | 1/1988 | Weiss |
| 4,723,121 A | 2/1988 | Van |
| 4,731,575 A | 3/1988 | Sloan |
| 4,737,770 A | 4/1988 | Brunius |
| 4,740,792 A | 4/1988 | Sagey |
| 4,750,118 A | 6/1988 | Heitschel |
| 4,754,255 A | 6/1988 | Sanders |
| 4,755,792 A | 7/1988 | Pezzolo |
| 4,758,835 A | 7/1988 | Rathmann |
| 4,761,808 A | 8/1988 | Howard |
| 4,779,090 A | 10/1988 | Micznik |
| 4,794,268 A | 12/1988 | Nakano |
| 4,794,622 A | 12/1988 | Isaacman |
| 4,796,181 A | 1/1989 | Wiedemer |
| 4,799,061 A | 1/1989 | Abraham |
| 4,800,590 A | 1/1989 | Vaughan |
| 4,802,114 A | 1/1989 | Sogame |
| 4,804,938 A | 2/1989 | Rouse |
| 4,807,052 A | 2/1989 | Amano |
| 4,808,995 A | 2/1989 | Clark |
| 4,825,200 A | 4/1989 | Evans |
| 4,825,210 A | 4/1989 | Bachhuber |
| 4,829,296 A | 5/1989 | Clark |
| 4,831,509 A | 5/1989 | Jones |
| 4,835,407 A | 5/1989 | Kataoka |
| 4,845,491 A | 7/1989 | Fascenda |
| 4,847,614 A | 7/1989 | Keller |
| 4,850,046 A | 7/1989 | Philippe |
| 4,855,713 A | 8/1989 | Brunius |
| 4,856,062 A | 8/1989 | Weiss |
| 4,856,081 A | 8/1989 | Smith |
| 4,859,990 A | 8/1989 | Isaacman |
| 4,870,400 A | 9/1989 | Downs |
| 4,878,052 A | 10/1989 | Schulze |
| 4,881,148 A | 11/1989 | Lambropoulos |
| 4,885,778 A | 12/1989 | Weiss |
| 4,888,575 A | 12/1989 | De Vaulx |
| 4,890,108 A | 12/1989 | Drori |
| 4,893,338 A | 1/1990 | Pastor |
| 4,905,279 A | 2/1990 | Nishio |
| 4,910,750 A | 3/1990 | Fisher |
| 4,912,463 A | 3/1990 | Li |
| 4,914,696 A | 4/1990 | Dudczak |
| 4,918,690 A | 4/1990 | Markkula |
| 4,922,168 A | 5/1990 | Waggamon |
| 4,922,533 A | 5/1990 | Philippe |
| 4,928,098 A | 5/1990 | Dannhaeuser |
| 4,931,789 A | 6/1990 | Pinnow |
| 4,939,792 A | 7/1990 | Urbish |
| 4,942,393 A | 7/1990 | Waraksa |
| 4,951,029 A | 8/1990 | Severson |
| 4,963,876 A | 10/1990 | Sanders |
| 4,979,832 A | 12/1990 | Ritter |
| 4,980,913 A | 12/1990 | Skret |
| 4,988,990 A | 1/1991 | Warrior |
| 4,988,992 A | 1/1991 | Heitschel |
| 4,992,783 A | 2/1991 | Zdunek |
| 4,999,622 A | 3/1991 | Amano |
| 5,001,332 A | 3/1991 | Schrenk |
| 5,021,776 A | 6/1991 | Anderson |
| 5,023,908 A | 6/1991 | Weiss |
| 5,049,867 A | 9/1991 | Stouffer |
| 5,055,701 A | 10/1991 | Takeuchi |
| 5,058,161 A | 10/1991 | Weiss |
| 5,060,263 A | 10/1991 | Bosen |

(56) References Cited

U.S. PATENT DOCUMENTS

| | | |
|---|---|---|
| 5,091,942 A | 2/1992 | Dent |
| 5,103,221 A | 4/1992 | Memmola |
| 5,107,258 A | 4/1992 | Soum |
| 5,126,959 A | 6/1992 | Kurihara |
| 5,136,548 A | 8/1992 | Claar |
| 5,144,667 A | 9/1992 | Pogue |
| 5,146,067 A | 9/1992 | Sloan |
| 5,148,159 A | 9/1992 | Clark |
| 5,150,464 A | 9/1992 | Sidhu |
| 5,153,581 A | 10/1992 | Hazard |
| 5,159,329 A | 10/1992 | Lindmayer |
| 5,168,520 A | 12/1992 | Weiss |
| 5,193,210 A | 3/1993 | Nicholas |
| 5,197,061 A | 3/1993 | Halbert-Lassalle |
| 5,224,163 A | 6/1993 | Gasser |
| 5,237,614 A | 8/1993 | Weiss |
| 5,252,960 A | 10/1993 | Duhame |
| 5,278,907 A | 1/1994 | Snyder |
| 5,280,527 A | 1/1994 | Gullman |
| 5,331,325 A | 7/1994 | Miller |
| 5,361,062 A | 11/1994 | Weiss |
| 5,363,448 A | 11/1994 | Koopman |
| 5,365,225 A | 11/1994 | Bachhuber |
| 5,367,572 A | 11/1994 | Weiss |
| 5,369,706 A | 11/1994 | Latka |
| 5,412,379 A | 5/1995 | Waraksa |
| 5,414,418 A | 5/1995 | Andros |
| 5,420,925 A | 5/1995 | Michaels |
| 5,442,340 A | 8/1995 | Dykema |
| 5,442,341 A | 8/1995 | Lambropoulos |
| 5,444,737 A | 8/1995 | Cripps |
| 5,463,376 A | 10/1995 | Stoffer |
| 5,471,668 A | 11/1995 | Soenen |
| 5,473,318 A | 12/1995 | Martel |
| 5,479,512 A | 12/1995 | Weiss |
| 5,485,519 A | 1/1996 | Weiss |
| 5,517,187 A | 5/1996 | Bruwer |
| 5,528,621 A | 6/1996 | Heiman |
| 5,530,697 A | 6/1996 | Watanabe |
| 5,554,977 A | 9/1996 | Jablonski |
| RE35,364 E | 10/1996 | Heitschel |
| 5,563,600 A | 10/1996 | Miyake |
| 5,565,812 A | 10/1996 | Soenen |
| 5,566,359 A | 10/1996 | Corrigan |
| 5,576,701 A | 11/1996 | Heitschel |
| 5,578,999 A | 11/1996 | Matsuzawa |
| 5,594,429 A | 1/1997 | Nakahara |
| 5,598,475 A | 1/1997 | Soenen |
| 5,600,653 A | 2/1997 | Chitre |
| 5,608,723 A | 3/1997 | Felsenstein |
| 5,635,913 A | 6/1997 | Willmott |
| 5,657,388 A | 8/1997 | Weiss |
| 5,673,017 A | 9/1997 | Dery |
| 5,678,213 A | 10/1997 | Myer |
| 5,680,131 A | 10/1997 | Utz |
| 5,686,904 A | 11/1997 | Bruwer |
| 5,699,065 A | 12/1997 | Murray |
| 5,719,619 A | 2/1998 | Hattori et al. |
| 5,745,068 A | 4/1998 | Takahashi |
| 5,774,065 A | 6/1998 | Mabuchi |
| 5,778,348 A | 7/1998 | Manduley |
| 5,838,747 A | 11/1998 | Matsumoto |
| 5,872,519 A | 2/1999 | Issa |
| 5,898,397 A | 4/1999 | Murray |
| 5,923,758 A | 7/1999 | Khamharn |
| 5,936,999 A | 8/1999 | Keskitalo |
| 5,937,065 A | 8/1999 | Simon |
| 5,942,985 A | 8/1999 | Chin |
| 5,949,349 A | 9/1999 | Farris |
| 6,012,144 A | 1/2000 | Pickett |
| 6,049,289 A | 4/2000 | Waggamon |
| 6,052,408 A | 4/2000 | Trompower |
| 6,070,154 A | 5/2000 | Tavor |
| 6,094,575 A | 7/2000 | Anderson et al. |
| 6,154,544 A | 11/2000 | Farris |
| 6,157,719 A | 12/2000 | Wasilewski |
| 6,166,650 A | 12/2000 | Bruwer |
| 6,175,312 B1 | 1/2001 | Bruwer |
| 6,181,255 B1 | 1/2001 | Crimmins |
| 6,243,000 B1 | 6/2001 | Tsui |
| 6,275,519 B1 | 8/2001 | Hendrickson |
| 6,414,587 B1 | 7/2002 | Fitzgibbon |
| 6,414,986 B1 | 7/2002 | Usui |
| 6,456,726 B1 | 9/2002 | Yu |
| 6,463,538 B1 | 10/2002 | Elteto |
| 6,496,477 B1 | 12/2002 | Perkins |
| 6,535,544 B1 | 3/2003 | Partyka |
| 6,549,949 B1 | 4/2003 | Bowman-Amuah |
| 6,640,244 B1 | 10/2003 | Bowman-Amuah |
| 6,688,518 B1 | 2/2004 | Valencia |
| 6,690,796 B1 | 2/2004 | Farris |
| 6,697,379 B1 | 2/2004 | Jacquet |
| 6,754,266 B2 | 6/2004 | Bahl |
| 6,810,123 B2 | 10/2004 | Farris |
| 6,829,357 B1 | 12/2004 | Alrabady |
| 6,850,910 B1 | 2/2005 | Yu |
| 6,930,983 B2 | 8/2005 | Perkins |
| 6,956,460 B2 | 10/2005 | Tsui |
| 6,963,561 B1 | 11/2005 | Lahat |
| 6,980,518 B1 | 12/2005 | Sun |
| 6,980,655 B2 | 12/2005 | Farris |
| 6,988,977 B2 | 2/2006 | Gregori |
| 6,998,977 B2 | 2/2006 | Gregori |
| 7,002,490 B2 | 2/2006 | Lablans |
| 7,039,397 B2 | 5/2006 | Chuey |
| 7,039,809 B1 | 5/2006 | Wankmueller |
| 7,042,363 B2 | 5/2006 | Katrak |
| 7,050,479 B1 | 5/2006 | Kim |
| 7,050,794 B2 | 5/2006 | Chuey et al. |
| 7,057,494 B2 | 6/2006 | Fitzgibbon |
| 7,057,547 B2 | 6/2006 | Olmsted |
| 7,068,181 B2 | 6/2006 | Chuey |
| 7,071,850 B1 | 7/2006 | Fitzgibbon |
| 7,088,218 B2 | 8/2006 | Chuey |
| 7,088,706 B2 | 8/2006 | Zhang et al. |
| 7,139,398 B2 | 11/2006 | Candelore |
| 7,161,466 B2 | 1/2007 | Chuey |
| 7,298,721 B2 | 11/2007 | Atarashi et al. |
| 7,301,900 B1 | 11/2007 | Laksono |
| 7,332,999 B2 | 2/2008 | Fitzgibbon |
| 7,333,615 B1 | 2/2008 | Jarboe |
| 7,336,787 B2 | 2/2008 | Unger |
| 7,346,163 B2 | 3/2008 | Pedlow |
| 7,353,499 B2 | 4/2008 | De Jong |
| 7,406,553 B2 | 7/2008 | Edirisooriya et al. |
| 7,412,056 B2 | 8/2008 | Farris |
| 7,415,618 B2 | 8/2008 | De Jong |
| 7,429,898 B2 | 9/2008 | Akiyama |
| 7,447,498 B2 | 11/2008 | Chuey et al. |
| 7,489,922 B2 | 2/2009 | Chuey |
| 7,492,898 B2 | 2/2009 | Farris et al. |
| 7,492,905 B2 | 2/2009 | Fitzgibbon |
| 7,516,325 B2 | 4/2009 | Willey |
| 7,535,926 B1 | 5/2009 | Deshpande |
| 7,545,942 B2 | 6/2009 | Cohen et al. |
| 7,548,153 B2 | 6/2009 | Gravelle et al. |
| 7,561,075 B2 | 7/2009 | Fitzgibbon |
| 7,564,827 B2 | 7/2009 | Das et al. |
| 7,598,855 B2 | 10/2009 | Scalisi et al. |
| 7,623,663 B2 | 11/2009 | Farris |
| 7,668,125 B2 | 2/2010 | Kadous |
| 7,741,951 B2 | 6/2010 | Fitzgibbon |
| 7,742,501 B2 | 6/2010 | Williams |
| 7,757,021 B2 | 7/2010 | Wenzel |
| 7,764,613 B2 | 7/2010 | Miyake et al. |
| 7,786,843 B2 | 8/2010 | Witkowski |
| 7,812,739 B2 | 10/2010 | Chuey |
| 7,839,851 B2 | 11/2010 | Kozat |
| 7,855,633 B2 | 12/2010 | Chuey |
| 7,999,656 B2 | 8/2011 | Fisher |
| 8,014,377 B2 | 9/2011 | Zhang et al. |
| 8,130,079 B2 | 3/2012 | Mcquaide, Jr. et al. |
| 8,194,856 B2 | 6/2012 | Farris |
| 8,207,818 B2 | 6/2012 | Keller, Jr. |

(56) References Cited

U.S. PATENT DOCUMENTS

| | | |
|---|---|---|
| 8,209,550 B2 | 6/2012 | Gehrmann |
| 8,225,094 B2 | 7/2012 | Willey |
| 8,233,625 B2 | 7/2012 | Farris |
| 8,266,442 B2 | 9/2012 | Burke |
| 8,276,185 B2 | 9/2012 | Messina et al. |
| 8,284,021 B2 | 10/2012 | Farris et al. |
| 8,290,465 B2 | 10/2012 | Ryu et al. |
| 8,416,054 B2 | 4/2013 | Fitzgibbon |
| 8,422,667 B2 | 4/2013 | Fitzgibbon |
| 8,452,267 B2 | 5/2013 | Friman |
| 8,463,540 B2 | 6/2013 | Hannah et al. |
| 8,536,977 B2 | 9/2013 | Fitzgibbon |
| 8,544,523 B2 | 10/2013 | Mays |
| 8,581,695 B2 | 11/2013 | Carlson et al. |
| 8,615,562 B1 | 12/2013 | Huang et al. |
| 8,633,797 B2 | 1/2014 | Farris et al. |
| 8,634,777 B2 | 1/2014 | Ekbatani et al. |
| 8,645,708 B2 | 2/2014 | Labaton |
| 8,661,256 B2 | 2/2014 | Willey |
| 8,699,704 B2 | 4/2014 | Liu et al. |
| 8,760,267 B2 | 6/2014 | Bos et al. |
| 8,787,823 B2 | 7/2014 | Justice et al. |
| 8,830,925 B2 | 9/2014 | Kim et al. |
| 8,836,469 B2 | 9/2014 | Fitzgibbon et al. |
| 9,082,293 B2 | 7/2015 | Wellman et al. |
| 9,124,424 B2 | 9/2015 | Aldis |
| 9,142,064 B2 | 9/2015 | Muetzel et al. |
| 9,148,409 B2 | 9/2015 | Fitzgibbon |
| 9,160,408 B2 | 10/2015 | Krohne et al. |
| 9,280,704 B2 | 3/2016 | Lei et al. |
| 9,317,983 B2 | 4/2016 | Ricci |
| 9,336,637 B2 | 5/2016 | Neil et al. |
| 9,396,376 B1 | 7/2016 | Narayanaswami |
| 9,413,453 B2 | 8/2016 | Sugitani et al. |
| 9,418,326 B1 | 8/2016 | Narayanaswami |
| 10,862,924 B2 | 12/2020 | Fitzgibbon |
| RE48,433 E | 2/2021 | Fitzgibbon |
| 10,944,559 B2 | 3/2021 | Fitzgibbon |
| 2001/0023483 A1 | 9/2001 | Kiyomoto |
| 2002/0034303 A1 | 3/2002 | Farris |
| 2002/0184504 A1 | 12/2002 | Hughes |
| 2002/0191785 A1 | 12/2002 | Mcbrearty |
| 2002/0191794 A1 | 12/2002 | Farris |
| 2003/0056001 A1 | 3/2003 | Mate |
| 2003/0070092 A1 | 4/2003 | Hawkes |
| 2003/0072445 A1 | 4/2003 | Kuhlman |
| 2003/0147536 A1 | 8/2003 | Andivahis |
| 2003/0177237 A1 | 9/2003 | Stebbings |
| 2003/0191949 A1 | 10/2003 | Odagawa |
| 2003/0227370 A1 | 12/2003 | Brookbank |
| 2004/0019783 A1 | 1/2004 | Hawkes |
| 2004/0081075 A1 | 4/2004 | Tsukakoshi |
| 2004/0174856 A1 | 9/2004 | Brouet |
| 2004/0179485 A1 | 9/2004 | Terrier |
| 2004/0181569 A1 | 9/2004 | Attar |
| 2005/0053022 A1 | 3/2005 | Zettwoch |
| 2005/0058153 A1 | 3/2005 | Santhoff |
| 2005/0101314 A1 | 5/2005 | Levi |
| 2005/0174242 A1 | 8/2005 | Cohen |
| 2005/0285719 A1 | 12/2005 | Stephens |
| 2006/0083187 A1 | 4/2006 | Dekel |
| 2006/0109978 A1 | 5/2006 | Farris |
| 2006/0176171 A1 | 8/2006 | Fitzgibbon |
| 2007/0005806 A1 | 1/2007 | Fitzgibbon |
| 2007/0006319 A1 | 1/2007 | Fitzgibbon |
| 2007/0018861 A1 | 1/2007 | Fitzgibbon |
| 2007/0058811 A1 | 3/2007 | Fitzgibbon |
| 2007/0245147 A1 | 10/2007 | Okeya |
| 2008/0229400 A1 | 9/2008 | Burke |
| 2008/0297370 A1 | 12/2008 | Farris |
| 2009/0016530 A1 | 1/2009 | Farris |
| 2009/0021348 A1 | 1/2009 | Farris |
| 2009/0096621 A1 | 4/2009 | Ferlitsch |
| 2009/0176451 A1 | 7/2009 | Yang et al. |
| 2009/0315672 A1 | 12/2009 | Nantz et al. |
| 2010/0060413 A1 | 3/2010 | Fitzgibbon et al. |
| 2010/0112979 A1 | 5/2010 | Chen et al. |
| 2010/0125509 A1 | 5/2010 | Kranzley et al. |
| 2010/0125516 A1 | 5/2010 | Wankmueller et al. |
| 2010/0199092 A1 | 8/2010 | Andrus et al. |
| 2010/0211779 A1 | 8/2010 | Sundaram |
| 2011/0051927 A1 | 3/2011 | Murray et al. |
| 2011/0296185 A1 | 12/2011 | Kamarthy et al. |
| 2011/0316668 A1 | 12/2011 | Laird |
| 2011/0316688 A1 | 12/2011 | Ranjan |
| 2011/0317835 A1 | 12/2011 | Laird |
| 2011/0320803 A1 | 12/2011 | Hampel et al. |
| 2012/0054493 A1 | 3/2012 | Bradley |
| 2012/0297681 A1 | 11/2012 | Krupke et al. |
| 2013/0170639 A1 | 7/2013 | Fitzgibbon |
| 2013/0268333 A1 | 10/2013 | Ovick et al. |
| 2013/0272520 A1 | 10/2013 | Noda et al. |
| 2014/0169247 A1 | 6/2014 | Jafarian et al. |
| 2014/0289528 A1 | 9/2014 | Baghdasaryan |
| 2015/0222517 A1 | 8/2015 | Mclaughlin et al. |
| 2015/0358814 A1 | 12/2015 | Roberts |
| 2016/0021140 A1 | 1/2016 | Fitzgibbon |
| 2016/0198391 A1 | 7/2016 | Orthmann et al. |
| 2016/0261572 A1 | 9/2016 | Liu et al. |

FOREIGN PATENT DOCUMENTS

| | | |
|---|---|---|
| AU | 2006200340 | 8/2006 |
| AU | 2007203558 B2 | 2/2008 |
| AU | 2008202369 A1 | 1/2009 |
| AU | 2011202656 A1 | 1/2012 |
| AU | 2011218848 A1 | 9/2012 |
| CA | 2087722 C | 7/1998 |
| CA | 2193846 C | 2/2004 |
| CA | 2177410 C | 4/2008 |
| CA | 2443452 C | 7/2008 |
| CA | 2684658 A1 | 10/2008 |
| CA | 2708000 A1 | 12/2010 |
| CA | 2456680 C | 2/2011 |
| CA | 2742018 A1 | 12/2011 |
| CA | 2565505 C | 9/2012 |
| CA | 2631076 C | 9/2013 |
| CA | 2790940 C | 6/2014 |
| CA | 2596188 C | 7/2016 |
| CN | 101399825 A | 4/2009 |
| DE | 3234538 A1 | 3/1984 |
| DE | 3234539 A1 | 3/1984 |
| DE | 3244049 A1 | 9/1984 |
| DE | 3309802 A1 | 9/1984 |
| DE | 3309802 C2 | 9/1984 |
| DE | 3320721 | 12/1984 |
| DE | 3332721 A1 | 3/1985 |
| DE | 3407436 A1 | 8/1985 |
| DE | 3407469 A1 | 9/1985 |
| DE | 3532156 A1 | 3/1987 |
| DE | 3636822 C1 | 10/1987 |
| DE | 4204463 | 8/1992 |
| EP | 0043270 A1 | 1/1982 |
| EP | 0103790 A2 | 3/1984 |
| EP | 0154019 A1 | 9/1985 |
| EP | 0155378 A1 | 9/1985 |
| EP | 0244322 | 11/1987 |
| EP | 0244332 B1 | 11/1987 |
| EP | 0311112 A2 | 4/1989 |
| EP | 0335912 | 10/1989 |
| EP | 0372285 | 6/1990 |
| EP | 0265935 B1 | 5/1991 |
| EP | 0459781 | 12/1991 |
| EP | 0857842 | 8/1998 |
| EP | 0937845 A1 | 8/1999 |
| EP | 1024626 A1 | 8/2000 |
| EP | 1223700 | 7/2002 |
| EP | 1313260 | 5/2003 |
| EP | 1421728 A1 | 5/2004 |
| EP | 1625560 A1 | 2/2006 |
| EP | 1760985 A2 | 3/2007 |
| EP | 0771498 B1 | 5/2007 |
| EP | 1865656 A1 | 12/2007 |
| EP | 2293478 A2 | 3/2011 |

(56) References Cited

FOREIGN PATENT DOCUMENTS

| | | | |
|---|---|---|---|
| EP | 2149103 B1 | 12/2011 | |
| EP | 2437212 A1 | 4/2012 | |
| EP | 1875333 B1 | 1/2013 | |
| EP | 2290872 B1 | 6/2014 | |
| EP | 2800403 A1 | 11/2014 | |
| FR | 2606232 | 5/1988 | |
| FR | 2607544 | 6/1988 | |
| FR | 2685520 | 6/1993 | |
| FR | 2737373 | 1/1997 | |
| GB | 218774 | 7/1924 | |
| GB | 1156279 | 6/1969 | |
| GB | 2023899 | 1/1980 | |
| GB | 2051442 | 1/1981 | |
| GB | 2099195 | 12/1982 | |
| GB | 2118614 | 11/1983 | |
| GB | 2131992 | 6/1984 | |
| GB | 2133073 | 7/1984 | |
| GB | 2184774 | 7/1987 | |
| GB | 2254461 | 10/1992 | |
| GB | 2265482 | 9/1993 | |
| GB | 2288261 | 10/1995 | |
| GB | 2430115 | 3/2007 | |
| GB | 2440816 | 2/2008 | |
| GB | 2453383 A | 4/2009 | |
| JP | H6205474 | 7/1994 | |
| JP | 09322274 | 12/1997 | |
| WO | 9300137 | 1/1993 | |
| WO | 9301140 | 1/1993 | |
| WO | 9320538 | 10/1993 | |
| WO | 9400147 | 1/1994 | |
| WO | 9411829 | 5/1994 | |
| WO | 9418036 | 8/1994 | |
| WO | 0010301 | 2/2000 | |
| WO | 0010302 | 2/2000 | |
| WO | 03010656 | 2/2003 | |
| WO | 03079607 A1 | 9/2003 | |
| ZA | 8908225 | 10/1991 | |

OTHER PUBLICATIONS

Abrams, and Podell, 'Tutorial Computer and Network Security,' District of Columbia: IEEE, 1987. pp. 1075-1081.
Abramson, Norman. 'The Aloha System-Another alternative for computer communications,' pp. 281-285, University of Hawaii, 1970.
Adams, Russ, Classified, data-scrambling program for Apple II, Info-World, vol. 5, No. 3; Jan. 31, 1988.
Alexi, Werner, et al. 'RSA and Rabin Functions: Certain Parts Are as Hard as the Whole', pp. 194-209, Siam Computing, vol. 14, No. 2, Apr. 1988.
Allianz: Allianz-Zentrum for Technik GmbH-Detailed Requirements for Fulfilling the Specification Profile for Electronically Coded OEM Immobilizers, Issue 22, (Jun. 1994 (Translation Jul. 5, 1994).
Anderson, Ross. 'Searching for the Optium Correlation Attack', pp. 137-143, Computer Laboratory, Pembroke Street, Cambridge CB2 3QG, Copyright 1995.
Arazi, Benjamin, Vehicular Implementations of Public Key Cryptographic Techniques, IEEE Transactions on Vehicular Technology, vol. 40, No. 3, Aug. 1991, 646-653.
Australian Examiners First Report on Patent Application No. 2006202850 dated Feb. 25, 2010.
Australian Patent Application No. 2017265017; First Examination Report dated Oct. 8, 2018; 4 pages.
Baran, P. Distribution Communications, vol. 9, 'Security Secrecy and Tamper-free Communications', Rand Corporation, 1964.
Barbaroux, Paul. 'Uniform Results in. Polynomial-Time Security', pp. 297-306, Advances in Cryptology-Eurocrypt 92, 1992.
Barlow, Mike, 'A Mathematical Word Block Cipher,' 12 Cryptologia 256-264 (1988).

Bellovin, S.M. 'Security Problems in the TCPIIP Protocol Suite', pp. 32-49, Computer Communication Review, New Jersey, Reprinted from Computer Communication Review, vol. 19, No. 2, pp. 32-48, Apr. 1989.
Beutelspacher, Albrecht. Advances in Cryptology—Eurocrypt 87: 'Perfect and Essentially Perfect Authentication Schemes' (Extended Abstract), pp. 167-170, Federal Republic of Germany, believed to be publicly available prior to Jun. 30, 2004.
Bloch, Gilbert. Enigma Before Ultra Polish Work and the French Contribution, pp. 142-155, Cryptologia 11(3), (Jul. 1987).
Bosworth, Bruce, 'Codes, Ciphers, and Computers: An Introduction to Information Security' Hayden Book Company, Inc. 1982, pp. 30-54.
Brickell, Ernest F. and Stinson, Doug. 'Authentication Codes With Multiple Arbiters', pp. 51-55, Proceedings of Eurocrypt 88, 1988.
British Application No. GB1110709.1; Combined Search and Examination Report Under Sections 17 and 18(3); dated Sep. 29, 2011.
British Combined Search and Examination Report Under Sections 17 and 18(3); British Patent Application No. GB1000541.1; dated Jan. 28, 2010.
British Combined Search and Examination Report Under Sections 17 and 18(3); British Patent Application No. GB1104752.9; dated Apr. 11, 2011.
British Examination Report Under Section 17(5); British Application No. GB0715089.9 dated Nov. 28, 2007.
British Examination Report Under Section 18(3); British Patent Application No. GB0601795.8; dated Apr. 22, 2009.
British Examination Report Under Section 18(3); British Patent Application No. GB0613068.6; dated Nov. 26, 2010.
British Examination Report Under Section 18(3); British Patent Application No. GB0613068.6; dated May 6, 2010.
British Patent Application No. GB1110710.9; Combined Search and Examination Report Under Sections 17 and 18(3); Search dated Sep. 30, 2011.
British Search Report Under Section 17; British Patent Application No. GB0601795.8; Search dated May 22, 2006.
British Search Report Under Section 17; British Patent Application No. GB0613068.6; Search dated Aug. 23, 2006.
British Search Report Under Section 17; British Patent Application No. GB0715089.9; Search dated May 9, 2008.
British Search Report Under Section 17(5); British Patent Application No. GB0613068.6; Search dated Oct. 12, 2006.
British Search Report Under Section 18(3); British Patent Application No. GB0613068.6; dated Oct. 12, 2006.
Bruwer, Frederick J. 'Die Toepassing Van Gekombineerde Konvolusiekodering en Modulasie op HF-Datakommunikasie,' District of Pretoria in South Africa Jul. 1998.
Burger, Chris R., Secure Learning RKE Systems Using KeeLoq. RTM. Encoders, TB001, 1996 Microchip Technology, Inc., 1-7.
Burmeister, Mike. A Remark on the Effiency of Identification Schemes, pp. 493-495, Advances in Cryptology-Eurocrypt 90, (1990).
Canadian Patent Application No. 2,551,295; Office Action dated May 6, 2013.
Canadian Patent Application No. 2,926,281, Canadian Office Action dated Dec. 27, 2017.
Canadian Patent Application No. 2,926,281, Canadian Office Action dated Dec. 29, 2016.
Canadian Patent Application No. 2,926,281, Canadian Office Action dated Nov. 19, 2018.
Canadian Patent Application No. 3,074,762, Canadian Office Action dated May 10, 2021.
Cattermole, K.W., 'Principles of Pulse Code Modulation' Iliffe Books Ltd., 1969, pp. 30-381.
Cerf, Vinton a 'Issues in Packet-Network Interconnection', pp. 1386-1408, Proceedings of the IEEE, 66(11), Nov. 1978.
Cerf, Vinton G. and Kahn, Robert E. 'A Protocol for Packet Network Intercommunication', pp. 637-648, Transactions on Communications, vol. Com-22, No. 5, May 1974.
Charles Watts, How to Program the HiSec(TM) Remote Keyless Entry Rolling Code Generator, National Semiconductor, Oct. 1994, 1-4.

(56) References Cited

OTHER PUBLICATIONS

Combined Search and Examination Reports Under Sections 17 and 18(3); British Patent Application No. GB0920612.9; Search dated Dec. 16, 2009.
Computer Arithmetic by Henry Jacobowitz; Library of Congress Catalog Card No. 62-13396; Copyright Mar. 1962 by John F. Rider Publisher, Inc.
Conner, Doug, Cryptographic Techniques—Secure Your Wireless Designs, EDN (Design Feature), Jan. 18, 1996, 57-68.
Coppersmith, Don. 'Fast Evaluation of Logarithms in Fields of Characteristic Two', IT-30(4): pp. 587-594, IEEE Transactions on Information Theory, Jul. 1984.
Daniels, George, 'Pushbutton Controls for Garage Doors' Popular Science (Aug. 1959), pp. 156-160.
Davies, D.W. and Price, W.C. 'Security for Computer Networks,' John Wiley and Sons, 1984. Chapter 7, pp. 175-176.
Davies, Donald W., 'Tutorial: The Security of Data in Networks,' pp. 13-17, New York: IEEE, 1981.
Davis, Ben and De Long, Ron. Combined Remote Key Conrol and Immobilization System for Vehicle Security, pp. 125-132, Power Electronics in Transportation, IEEE Catalogue No. 96TH8184, (Oct. 24, 1996).
Davis, Gregory and Palmer, Morris. Self-Programming, Rolling-Code Technology Creates Nearly Unbreakable RF Security, Technological Horizons, Texas Instruments, Inc. (ECN), (Oct. 1996).
Deavours, C. A. and Reeds, James. The Enigma, Part 1, Historical Perspectives, pp. 381-391, Cryptologia, 1(4), (Oct. 1977).
Deavours, C.A. and Kruh, L. 'The Swedish HC-9 Ciphering Machine', 251-285, Cryptologia, 13(3): Jul. 1989.
Deavours, Cipher A., et al. 'Analysis of the Hebern cryptograph Using Isomorphs', pp. 246-261, Cryptology: Yesterday, Today and Tomorrow, vol. 1, No. 2, Apr. 1977.
Denning, Dorothy E. 'Cryptographic Techniques', pp. 135-154, Cryptography and Data Security, 1982. Chapter 3.
Denning, Dorothy E. A Lattice Model of Secure Information Flow, pp. 236-238, 240, 242, Communications of the ACM, vol. 19, No. 5, (May 1976).
Diffie and Hellman, Exhaustive Cryptanalysis of the NB.S Data Encryption Standard, pp. 74-84, Computer, Jun. 1977.
Diffie, Whitfield and Hellman, Martin E. New Directions in Cryptography, pp. 644-654, IEEE Transactions on Information Theory, vol. IT-22, No. 6, (Nov. 1976).
Diffie, Whitfield and Hellman, Marfin E. Privacy and Authentication: An Introduction to Cryptography, pp. 397-427, Proceedings of the IEEE, vol. 67, No. 3 (Mar. 1979).
Diffie, Whitfield and Hellman, Martin, E. 'An RSA Laboratories Technical Note', Version 1.4, Revised Nov. 1, 1993.
Dijkstra, E. W. Co-Operating Sequential Processses, pp. 43-112, Programming Languages, F. Genuys. NY, believed to be publicly available prior to Jun. 30, 2004.
Dijkstra, E.W. 'Hierarchical Ordering of Sequential Processes', pp. 115-138, Acta Informatica 1: 115-138, Springer-Verlag (1971).
Documents Having Confidential Information Cited by Third Party as Relevant to the Subject Matter (Obtained from Notice Pursuant to 35 U.S.C. .sctn.282, Mar. 4, 2011(NPL22)).
ElGamal, Taher. A Public Key Cryptosystem and a Signature Scheme Based on Discrete Logarithms, pp. 469-472, IEEE, Transactions on Information Theory, vol. IT-31, No. 4, (Jul. 1985).
ElGamal, Taher. A Subexponential Time Algorithm for Computing Discrete Logarithms, pp. 473-481, IEEE, Transactions on Information Theory, vol. IT-31, No. 4, (Jul. 1985).
Examination Report Under Section 18(3) for GB0502236.3 dated May 23, 2005.
Examination Report Under Section 18(3) From British Patent Application No. GB0601795.8; Search dated Jan. 28, 2010.
Examination Report Under Section 18(3) From British Patent Application No. GB0601795.8; Search dated Sep. 25, 2009.
Examination Report Under Section 18(3) From British Patent Application No. GB0613068.6; Search dated Jan. 31, 2011.
Examination Report Under Section 18(3) from British Patent Application No. GB0715089.9 dated Apr. 11, 2011.
Examination Report Under Section 18(3) From British Patent Application No. GB0715089.9; Search dated Sep. 30, 2010.
Examination Report Under Section 18(3) From British Patent Application No. GB0920612.9; Search dated Jan. 28, 2010.
Feistel, Horst, Notz, Wm. A. and Smith, J. Lynn. Some Cryptographic Techniques for Machine-to-Machine Data Communications, pp. 1545-1554, Proceedings of the IEEE, vol. 63, No. 11, (Nov. 1975).
Feistel, Horst. 'Cryptography and Computer Privacy', pp. 15-23, Scientific American, vol. 228, No. 5, May 1973.
Fenzl, H. and Kliner, A. Electronic Lock System: Convenient and Safe, pp. 150-153, Siemens Components XXI, No. 4, (1987).
First Examination Report, from Australian Application No. 2019240615, dated Aug. 13, 2020; 4 pages.
Fischer, Elliot. Uncaging the Hagelin Cryptograph, pp. 89-92, Cryptologia, vol. 7, No. 1, (Jan. 1983).
Fragano, Maurizio. Solid State Key/Lock Security System, pp. 604-607, IEEE Transactions on Consumer Electronics, vol. CE-30, No. 4, (Nov. 1984).
G. Davis, Marcstar.TM. TRC1300 and TRC1315 Remote Control Transmitter/Receiver, Texas Instruments, Sep. 12, 1994. 1-24.
German Patent Application No. 10 2006 003 808.3; Official Action dated May 16, 2018; 6 pages.
German Patent Application No. 10 2006 003 808.8; Official Action dated Feb. 14, 2019 (with translation of relevant parts); 6 pages.
German Patent Application No. 10 2006 003 808.8; Official Action dated Oct. 9, 2018 (with translation of relevant parts); 7 pages.
German Patent Application No. 10 2006 063 085.8; Official Action dated Nov. 7, 2019 (with translation of relevant parts); 14 pages.
German Patent Application No. 10 2007 036 647.9; Official Communication dated Jul. 4, 2019, 4 pages.
Godlewski, Ph. and Camion P. 'Manipulations and Errors, Delection and Localization,' pp. 97-106, Proceedings of Eurocrypt 88, 1988.
Gordon, Professor J., Police Scientific Development Branch, Designing Codes for Vehicle Remote Security Systems, (Oct. 1994), pp. 1-20.
Gordon, Professor J., Police Scientific Development Branch, Designing Rolling Codes for Vehicle Remote Security Systems, (Aug. 1993), pp. 1-19.
Greenlee, B.M., Requirements for Key Management Protocols in the Wholesale Financial Services Industry, pp. 22 28, IEEE Communications Magazine , Sep. 1985.
Guillou, Louis C. and Quisquater, Jean-Jacques. 'A Practical Zero-Knowledge Protocol Fitted to Security Microprocessor Minimizing Both Transmission and Memory', pp. 123-128, Advances in Cryptology-Eurocrypt 88, 1988.
Guillou, Louis C. Smart Cards and Conditional Access, pp. 481-489, Proceedings of Eurocrypt, (1984).
Habermann, A. Nico, Synchronization of Communicating Processes, pp. 171 176, Communications, Mar. 1972.
Hagelin C-35/C-36 (The), (1 page) Sep. 3, 1998. http://hem.passagen.se/tan01/C035.HTML.
Haykin, Simon, "An Introduction to Analog and Digital Communications" 213, 215 (1989).
IEEE 100; The Authoritative Dictionary of IEEE Standards Terms, Seventh Ediciton, Published by Standards Information Network, IEEE Press, Copyright 2000.
International Search Report for PCT/US03/25308 dated Mar. 25, 2004.
ISO 8732: 1988(E): Banking Key Management (Wholesale) Annex D: Windows and Windows Management, Nov. 1988.
ITC Tutorial; Investigation No. 337-TA-417; (TCG024374-24434); Dated: Jul. 7, 1999.
Jones, Anita K. Protection Mechanisms and the Enforcement of Security Policies, pp. 228-251, Carnegie-Mellon University, Pittsburgh, PA, (1978).
Jueneman, R.R. et al. 'Message Authentication', pp. 29-40, IEEE Communications Magazine, vol. 23, No. 9, Sep. 1985.
Kahn, Robert E. The Organization of Computer Resources Into a Packet Radio Network, pp. 177-186, National Computer Conference, (1975).

(56) References Cited

OTHER PUBLICATIONS

Keeloq.RTM. Code Hopping Decoder, HCS500, 1997 Microchip Technology, Inc., 1-25.
Keeloq.RTM. Code Hopping Encoder, HCS300, 1996 Microchip Technology, Inc., 1-20.
Keeloq.RTM. NTQ 105 Code Hopping Encoder, pp. 1-8, Nanoteq (Pty.) Ltd., (Jul. 1993).
Keeloq.RTM. NTQ 125D Code Hopping Decoder, pp. 1-9, Nanoteq (pty.) Ltd., (Jul. 1993).
Kent, Stephen T. A Comparison of Some Aspects of Public-Key and Conventional Cryptosystems, pp. 4.3.1-5, ICC '79 Int. Conf. on Communications, Boston, MA, (Jun. 1979).
Kent, Stephen T. Comments on 'Security Problems in the TCP/IP Protocol Suite', pp. 10-19, Computer Communication Review, vol. 19, Part 3, (Jul. 1989).
Kent, Stephen T. Encryption-Based Protection Protocols for Interactive User-Computer Communication, pp. 1-121, (May 1976). (See pp. 50-53).
Kent, Stephen T. Protocol Design Consideration for Network Security, pp. 239-259, Proc. NATO Advanced Study Institute on Interlinking of Computer Networks, (1979).
Kent, Stephen T. Security Requirements and Protocols for a Broadcast Scenario, pp. 778-786, IEEE Transactions on Communications, vol. com-29, No. 6, (Jun. 1981).
Kent, Stephen T., et al. Personal Authorization System for Access Control to the Defense Data Network, pp. 89-93, Conf. Record of Eascon 82 15.sup.th Ann Electronics & Aerospace Systems Conf., Washington, D.C. (Sep. 1982).
Konheim, A.G. Cryptography: A Primer, pp. 285-347, New York, (John Wiley, 1981).
Koren, Israel, "Computer Arithmetic Algorithms" Prentice Hall, 1978, pp. 1-15.
Kruh, Louis. Device anc Machines: The Hagelin Cryptographer, Type C-52, pp. 78-82, Cryptologia, vol. 3, No. 2, (Apr. 1979).
Kruh, Louis. How to Use the German Enigma Cipher Machine: A photographic Essay, pp. 291-296, Cryptologia, vol. No. 7, No. 4 (Oct. 1983).
Kuhn, G.J., et al. A Versatile High-Speed Encryption Chip, INFOSEC '90 SYMPOSIUM, Pretoria, (Mar. 16, 1990).
Kuhn. G.J. Algorithms for Self-Synchronizing Ciphers, pp. 159-164, Comsig 88, University of Pretoria, Pretoria, (1988).
Lamport, Leslie. The Synchronization of Independent Processes, pp. 15-34, Acta Informatica, vol. 7, (1976).
Lear Corporation's Memorandum of Law in Support of Its Motion for Summary Judgment; May 22, 2008.
Linn, John and Kent, Stephen T. Electronic Mail Privacy Enhancement, pp. 40-43, American Institute of Aeronautics and Astronautics, Inc. (1986).
Lloyd, Sheelagh. Counting Functions Satisfying a Higher Order Strict Avalanche Criterion, pp. 63-74, (1990).
Marneweck, Kobus. Guidelines for KeeLoq.RTM. Secure Learning Implementation, TB007, pp. 1-5, 1987 Microchip Technology, Inc.
Massey, James L. The Difficulty with Difficulty, pp. 1-4, Jul. 17, 1996. http://www.iacr.org/conferences/ec96/massey/html/framemassey.html.
McIvor, Robert. Smart Cards, pp. 152-159, Scientific American, vol. 253, No. 5, (Nov. 1985).
Meier, Willi. Fast Correlations Attacks on Stream Ciphers (Extended Abstract), pp. 301-314, Eurocrypt 88, IEEE, (1988).
Meyer, Carl H. and Matyas Stephen H. Cryptography: A New Dimension in Computer Data Security, pp. 237-249 (1982).
Michener, J.R. The 'Generalized Rotor' Cryptographic Operator and Some of Its Applications, pp. 97-113, Cryptologia, vol. 9, No. 2, (Apr. 1985).
Microchip Technology, Inc., Enhanced Flash Microcontrollers with 10-Bit A/D and nano Watt Technology, PIC18F2525/2620/4525/4620 Data Sheet, 28/40/44-Pin, .COPYRGT.2008.
Microchip v. *The Chamberlain Group, Inc.*, (TCG019794-019873); Deposition of J. Fitzgibbon; Partially redacted; Dated: Jan. 7, 1999.
Microchip v. *The Chamberlain Group, Inc.*, (TCG019874-019918); Deposition of J. Fitzgibbon; Dated: Mar. 16, 1999.
*Microchip v. The Chamberlain Group, Inc.*, Civil Action No. 98-C-6138; (TCG024334-24357); Declaration of V. Thomas Rhyne; Dated: Feb. 22, 1999.
MM57HS01 HiSeC.TM. Fixed and Rolling Code Decoder, National Semiconductor, Nov. 11, 1994, 1-8.
Morris, Robert. The Hagelin Cipher Machine (M-209): Reconstruction of the Internal Settings, pp. 267-289, Cryptologia, 2(3), (Jul. 1978).
Newman, David B., Jr., et al. 'Public Key Management for Network Security', pp. 11-16, IEE Network Magazine, 1987.
Nickels, Hamilton, 'Secrets of Making and Breading Codes' Paladin Press, 1990, pp. 11-29.
Niederreiter, Harald. Keystream Sequences with a Good Linear Complexity Profile for Every Starting Point, pp. 523-532, Proceedings of Eurocrypt 89, (1989).
NM95HSO1/NM95HSO2 HiSeC.TM. (High Security Code) Generator, pp. 1-19, National Semiconductor, (Jan. 1995).
Otway, Dave and Rees, Owen. Efficient and timely mutual authentication, ACM SIGOPS Operating Systems Review, vol. 21, Issue 1, Jan. 8-10, 1987.
Peebles, Jr., Peyton Z. and Giuma, Tayeb A.; "Principles of Electrical Engineering" McGraw Hill, Inc., 1991, pp. 562-597.
Peyret, Patrice, et al. Smart Cards Provide Very High Security and Flexibility in Subscribers Management, pp. 744-752, IEE Transactions on Consumer Electronics, 36(3), (Aug. 1990).
Postel, J. ed. 'DOD Standard Transmission Control Protocol', pp. 52-133, Jan. 1980.
Postel, Jonathon B., et al. The ARPA Internet Protocol, pp. 261-271, (1981).
Reed, David P. and Kanodia, Rajendra K. Synchronization with Eventcounts and Sequencers, pp. 115-123, Communications of the ACM, vol. 22, No. 2, (Feb. 1979).
Reynolds, J. and Postel, J. Official ARPA-Internet Protocols, Network Working Groups, (Apr. 1985).
Roden, Martin S., "Analog and Digital Communication Systems," Third Edition, Prentice Hall, 1979, pp. 282-460.
Ruffell, J. Battery Low Indicator, p. 15-165, Eleckton Electronics, (Mar. 1989). (See p. 59).
Saab Anti-Theft System: 'Saab's Engine Immobilizing Anti-Theft System is a Road-Block for 'Code-Grabbing' Thieves', pp. 1-2, Aug. 1996; http://www.saabusa.com/news/newsindex/alarm.html.
Savage. J.E. Some Simple Self-Synchronizing Digital Data Scramblers, pp. 449-498, The Bell System Tech. Journal, (Feb. 1967).
Search Report Under Section 17 From British Patent Application No. GB0601795.8; Search dated Apr. 22, 2009.
Search Report Under Section 17, Application No. GB0715089.9; Search dated Nov. 27, 2007.
Seberry, J. and Pieprzyk, Cryptography—An Introduction to Computer Security, Prentice Hall of Australia, YTY Ltd, 1989, pp. 134-136.
Second Examination Report, from Australian Application No. 2019240615, dated Apr. 28, 2021; 2 pages.
Secure Terminal Interface Module for Smart Card Application, pp. 1488-1489, IBM: Technical Disclosure Bulletin, vol. 28, No. 4, (Sep. 1985).
Shamir, Adi. 'Embedding Cryptographic Trapdoors in Arbitrary Knapsack Systems', pp. 77-79, Information Processing Letters, 1983.
Shamir, Adi. Embedding cryptographic Trapdoors in Arbitrary Knapsak Systems, pp. 81-85, IEEE Transactions on Computers, vol. C-34, No. 1, (Jan. 1985).
Siegenthaler, T. Decrypting a Class of Stream Ciphers Using Ciphertext Only, pp. 81-85, IEEE Transactions on Computers, vol. C-34, No. 1, (Jan. 1985).
Simmons, Gustavus, J. Message Authentication with Arbitration of Transmitter/Receiver Disputes, pp. 151-165 (1987).
Smith, J.L., et al. An Experimental Application of Crptography to a Remotely Accessed Data System, pp. 282-297, Proceedings of hte ACM, (Aug. 1972).
Smith, Jack, 'Modem Communication Circuits.' McGraw-Hill Book Company, 1986, Chapter 11, pp. 420-454.

(56) References Cited

OTHER PUBLICATIONS

Smith, Jack, 'Modem Communication Circuits' McGraw-Hill Book Company, 1986, Chapter 7, pp. 231-294.

Smith. J.L. The Design of Lucifer: a Cryptographic Device for Data Communications, pp. 1-65, (Apr. 15, 1971).

Soete, M. Some constructions for authentication—secrecy codes, Advances in Cryptology-Eurocrypt '88, Lecture Notes in Computer Science 303 (1988), 57-75.

Steven Dawson, Keelog.RTM. Code Hopping Decoder Using Secure Learn, AN662, 1997 Microchip Technology, Inc., 1-16.

Svigals, J. Limiting Access to Data in an Indentification Card Having a Micro-Processor, pp. 580-581, IBM: Technical Disclosre Bulletin, vol. 27, No. 1B, (Jun. 1984).

Thatcham: The Motor Insurance Repair Research Centre, The British Insurance Industry's Criteria for Vehicle Security (Jan. 1993) (Lear 18968-19027), pp. 1-36.

Transaction Completion Code Based on Digital Signatures, pp. 1109-1122, IBM: Technical Disclosure Bulletin, vol. 28, No. 3, (Aug. 1985).

Turn, Rein. Privacy Transformations for Databank Systems, pp. 589-601, National Computer Conference, (1973).

U.S. District Court, Northern District of Illinois, Eastern Division, Civil Action No. 05-C-3449, Declaration of Robert Louis Stevenson, Jr., Jun. 26, 2009.

U.S. District Court, Northern District of Illinois, Eastern Division, Civil Action No. 05-C-3449, JCI's Local Rule 56.1 Statement of Undisputed Facts in Support of Their Motion for Summary Judgment of Infringement of the '056 Patent; Jul. 6, 2009.

U.S. District Court, Northern District of Illinois, Eastern Division, Civil Action No. 05-C-3449, JCI's Local Rule 56.1 Statement of Undisputed Facts in Support of Their Motion for Summary Judgment of Infringement of the '544 Patent; Jul. 6, 2009.

U.S. District Court, Northern District of Illinois, Eastern Division, Civil Action No. 05-C-3449, JCI's Memorandum of Law in Support of its Motion for Summary Judgment of Infringement of the '056 Patent, Jul. 6, 2009.

U.S. District Court, Northern District of Illinois, Eastern Division, Civil Action No. 05-C-3449, JCI's Memorandum of Law in Support of its Motion for Summary Judgment of Infringement of the '544 Patent, Jul. 6, 2009.

U.S. District Court, Northern District of Illinois, Eastern Division, Civil Action No. 05-C-3449, Memorandum Opinion and Order, Nov. 24, 2010.

U.S. District Court, Northern District of Illinois, Eastern Division, Civil Action No. 05-CV-3449, Defendant Lear Corporation's Answer to Plaintiffs' Second Amended Complaint, Defenses, and Counterclaim; Sep. 8, 2008.

U.S. District Court, Northern District of Illinois, Eastern Division, Civil Action No. 05-CV-3449, Defendant Lear Corporation's Reply Memorandum in Support of Its Motion to Stay Effectiveness of Any Preliminary Injunction; Apr. 17, 2007.

U.S. District Court, Northern District of Illinois, Eastern Division, Civil Action No. 05-CV-3449, Lear Corporation Memorandum of Law in Support of Its Motion for Summary Judgment of U.S. Pat. No. 7,412,056; Dec. 8, 2008.

U.S. District Court, Northern District of Illinois, Eastern Division, Civil Action No. 05-CV-3449, Lear Corporation's Answer, Affirmative Defenses and Counterclaims to Plaintiffs' Amended Complaint; Oct. 24, 2005.

U.S. District Court, Northern District of Illinois, Eastern Division, Civil Action No. 05-CV-3449, Lear Corporation's Memorandum of Law in Support of Its Emergency Motion to Stay the Effectiveness of the Preliminary Injunction Memorandum Opinion and Order Entered Mar. 30, 2007.

U.S. District Court, Northern District of Illinois, Eastern Division, Civil Action No. 05-CV-3449, Lear Corporation's Memorandum of Law in Support of Its Motion for Summary Judgment, May 22, 2008.

U.S. District Court, Northern District of Illinois, Eastern Division, Civil Action No. 05-CV-3449, Lear Corporation's Motion for Reconsideration of the Court's Sep. 11, 2006 Memorandum Opinion and Order Regarding Claim Construction.

U.S. District Court, Northern District of Illinois, Eastern Division, Civil Action No. 05-CV-3449, Lear Corporation's Post-Markman Brief; Dated Jun. 15, 2006.

U.S. District Court, Northern District of Illinois, Eastern Division, Civil Action No. 05-CV-3449, Memorandum Opinion and Order, Apr. 25, 2007.

U.S. District Court, Northern District of Illinois, Eastern Division, Civil Action No. 05-CV-3449, Memorandum Opinion and Order, Feb. 20, 2007.

U.S. District Court, Northern District of Illinois, Eastern Division, Civil Action No. 05-CV-3449, Memorandum Opinion and Order, Sep. 11, 2006.

U.S. District Court, Northern District of Illinois, Eastern Division, Civil Action No. 05-CV-3449, Memorandum Opinion and Order; Mar. 30, 2007.

U.S. District Court, Northern District of Illinois, Eastern Division, Civil Action No. 05-CV-3449, Notice of Motion and Motion for Leave to File Defendant Lear Corporation's Sur-Reply to Chamberlain's and JCI's Reply Memorandum in Support of Motion for Preliminary Injunction; Mar. 30, 2006.

U.S. District Court, Northern District of Illinois, Eastern Division, Civil Action No. 05-CV-3449, Plaintiffs' Opposition to Lear Corporation's Motion to Stay the Effectiveness of the Preliminary Injunction Memorandum Opinion and Order Entered Mar. 30, 2007.

U.S. District Court, Northern District of Illinois, Eastern Division, Civil Action No. 05-CV-3449, Plaintiffs' Response to Lear's Mar. 2, 2007 Supplemental Memorandum.

U.S. District Court, Northern District of Illinois, Eastern Division, Civil Action No. 05-CV-3449, Plaintiffs' Response to Lear's Motion for Reconsideration of the Court's Sep. 11, 2006 Ruling Regarding Claim Construction; Oct. 4, 2006.

U.S. District Court, Northern District of Illinois, Eastern Division, Civil Action No. 05-CV-3449, Plaintiffs' Surreply Memorandum in Opposition to Lear's Motion to Stay the Preliminary Injunction, Apr. 24, 2007.

U.S. District Court, Northern District of Illinois, Eastern Division, Civil Action No. 05-CV-3449, Plaintiffs' Surreply Memorandum in Support of Motion for Preliminary Injunction.

U.S. District Court, Northern District of Illinois, Eastern Division, Civil Action No. 05-CV-3449, Reply Brief in Support of Lear's Motion for Reconsideration of the Court's Sep. 11, 2006 Ruling Regarding Claim Construction.

U.S. District Court, Northern District of Illinois, Eastern Division, Civil Action No. 05-CV-3449, Supplemental Memorandum in Support of Defendant Lear Corporation's Opposition to Plaintiffs' Motion for Preliminary Injunction; Mar. 2, 2007.

U.S. District Court, Northern District of Illinois, Eastern Division, Civil Action No. 05-CV-3449, Transcript of Deposition of Bradford L. Farris, Jan. 12, 2006.

U.S. District Court, Northern District of Illinois, Eastern Division, Civil Action No. 05-CV-3449, Transcript of Deposition of Hubert E. Dunsmore, Jan. 12, 2006.

U.S. District Court, Northern District of Illinois, Eastern Division, Civil Action No. 05-CV-3449, Transcript of Proceedings Before the Honorable James B. Moran, May 31, 2005.

U.S. District Court, Northern District of Illinois, Eastern Division, Civil Action No. 05-CV-3449, Transcript of Proceedings Before the Honorable James B. Moran, May 31, 2006.

United States Court of Appeals for the Federal Circuit, Appeal from the United States District Court for the Northern District of Illinois in Case No. 05-CV-3449, Brief of Defendant—Appellant Lear Corporation.

United States Court of Appeals for the Federal Circuit, Appeal from the United States District Court for the Northern District of Illinois in Case No. 05-CV-3449, Brief of the Chamberlain Group, Inc. and Johnson Controls Interiors LLC; Aug. 8, 2007.

United States Court of Appeals for the Federal Circuit, Appeal from the United States District Court for the Northern District of Illinois in Case No. 05-CV-3449, Combined Petition for Panel Rehearing and Rehearing En Banc of Chamberlain Group, Inc.and Johnson Controls Interiors LLC; Dated Mar. 19, 2008.

(56) References Cited

OTHER PUBLICATIONS

United States Court of Appeals for the Federal Circuit, Appeal from the United States District Court for the Northern District of Illinois in Case No. 05-CV-3449, Reply Brief of Defendant—Appellant Lear Corporation, Aug. 29, 2007.
United States Court of Appeals for the Federal Circuit, Appeal from the United States District Court, Northern District of Illinois in Case No. 05-CV-3449, Appellate Decision, Feb. 19, 2008.
United States Court, Northern District of Illinois, Eastern Division, Civil Action 05 C 3449, Notice Pursuant to 35 U.S.C. 282, Mar. 4, 2011.
United States International Trade Commission in the Matter of Certain Code Hopping Remote Control Systems, Including Components and Integrated Circuits Used Therein; Investigation No. 337-TA-417; Expert Report of Dr. V. Thomas Rhyne; (TCG019919-19959); Partially redacted; Dated Jul. 7, 1999.
United States International Trade Commission, Washington, D., Investigation No. 337-TA-417; Respondents' Answer to Complaint and Notice of Investigation, Jan. 26, 1999.
U.S. Appl. No. 13/777,787; Notice of Allowance dated Sep. 11, 2020; (pp. 1-5).
U.S. Appl. No. 13/777,787; Notice of Allowance dated Oct. 16, 2020; (pp. 1-5).
U.S. Appl. No. 14/867,633; Corrected Notice of Allowability dated Oct. 27, 2020; (pp. 1-2).
U.S. Appl. No. 14/867,633; Notice of Allowance dated Aug. 10, 2020; (pp. 1-8).
U.S. Appl. No. 15/674,069; Notice of Allowance dated Sep. 30, 2020; (pp. 1-12).
U.S. Appl. No. 14/867,633; Notice of Allowance dated Apr. 1, 2020; (pp. 1-8).
U.S. Appl. No. 11/172,524; Office Action dated Apr. 9, 2009, (pp. 1-13).
U.S. Appl. No. 11/172,525; Office Action dated Apr. 9, 2009; (17 pages).
U.S. Appl. No. 11/172,525; Office Action dated Mar. 21, 2011; (42 pages).
U.S. Appl. No. 14/857,633; Office Action dated Jul. 19, 2018, (22 pages).
U.S. Appl. No. 14/867,633; Office Action dated Sep. 17, 2019; (pp. 1-25).
U.S. Appl. No. 15/674,069; Office Action dated May 8, 2020, (pp. 1-9).
Voydock, Victor L. and Kent, Stephen T. 'Security in High-Level Network Protocols', IEEE Communications Magazine, pp. 12-25, vol. 23, No. 7, Jul. 1985.
Voydock, Victor L. and Kent, Stephen T. 'Security Mechanisms in High-Level Network Protocols', Computing Surveys, pp. 135-171, vol. 15, No. 2, Jun. 1983.
Voydock, Victor L. and Kent, Stephen T. Security Mechanisms in a Transport Layer Protocol, pp. 325-341, Computers & Security, (1985).
Watts, Charles and Harper John. How to Design a HiSec.TM. Transmitter, pp. 1-4, National Semiconductor, (Oct. 1994).
Weinstein, S.B. Smart Credit Cards: The Answer to Cashless Shopping, pp. 43-49, IEEE Spectrum, (Feb. 1984).
Weissman, C. Securtiy Controls in the ADEPT-50 Time-Sharing Syustem, pp. 119-133, AFIPS Full Joint Compuer Conference, (1969).
Welsh, Dominic, Codes and Cryptography, pp. 7.0-7.1, (Clarendon Press, 1988).
Wolfe, James Raymond, "Secret Writing—The Craft of the Cryptographer" McGraw-Hill Book Company 1970, pp. 111-122, Chapter 10.
First Examination Report from Australian Application No. 2021277691, dated Jan. 16, 2023, 3 pages.

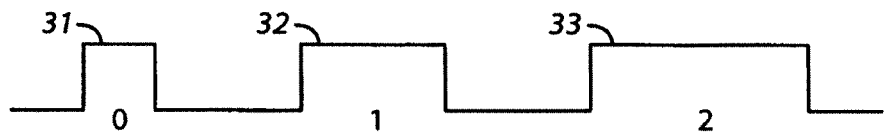
FIG. 3
*(Prior Art)*
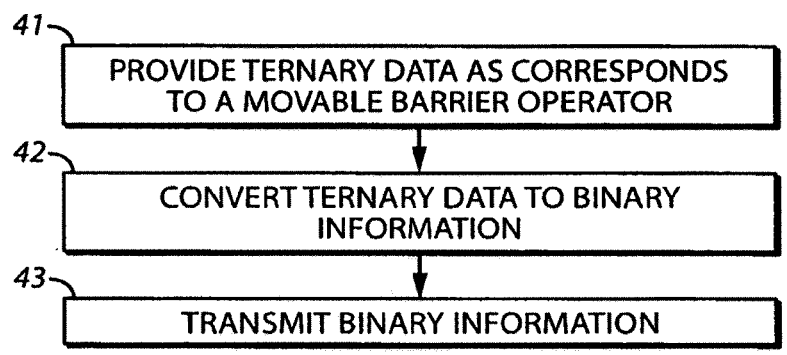
FIG. 4
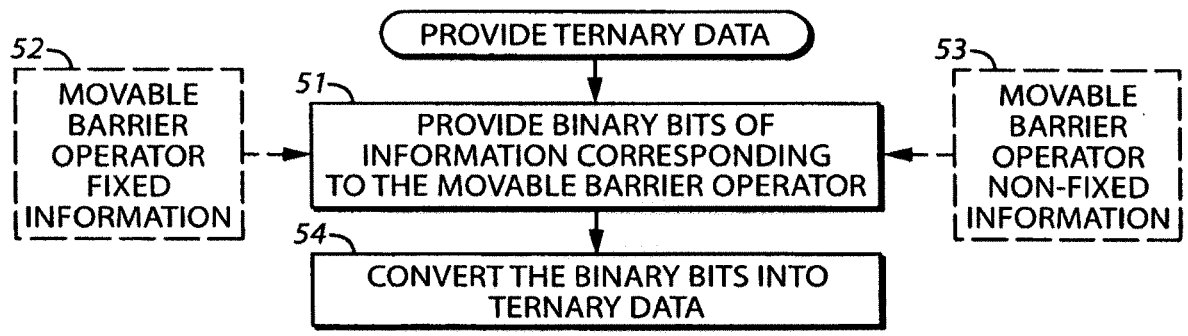
FIG. 5
| TERNARY DATA | BINARY BIT PAIRS |
|---|---|
| 0 | 00 |
| 1 | 01 |
| 2 | 10 |
| ILLEGAL | 11 |
FIG. 6

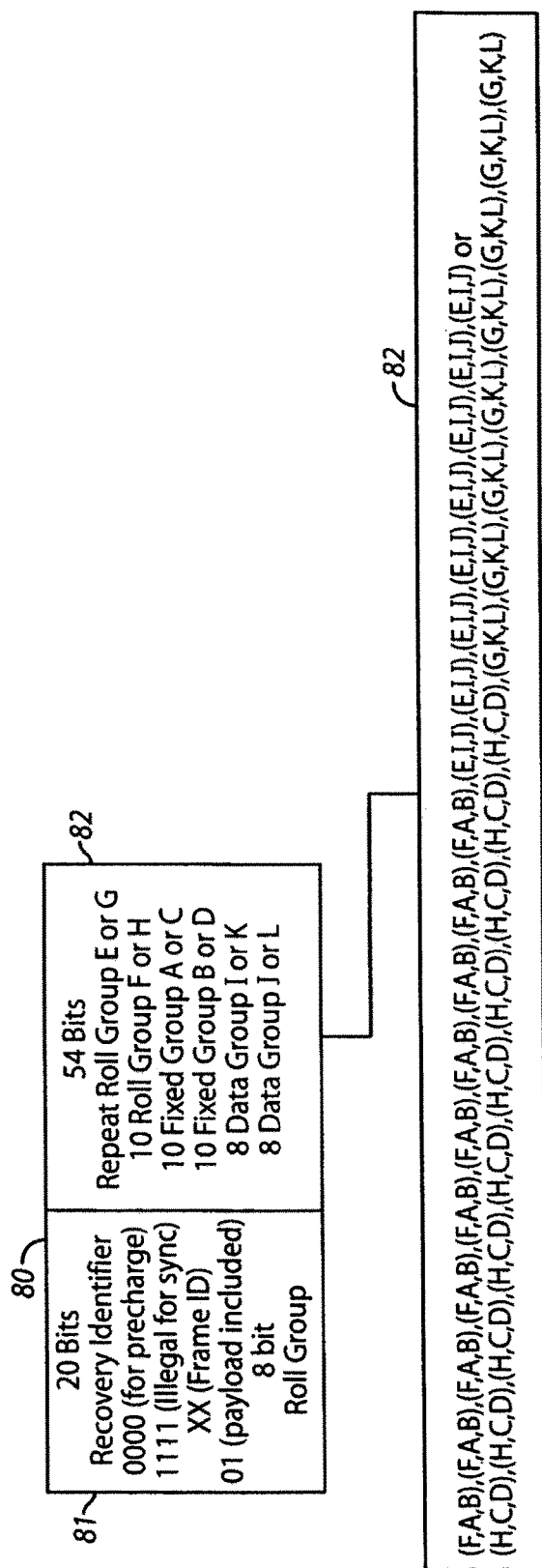

| B7 | B6 | B5 | B4 | Order of bits | B3 | B2 | B1 | B0 | Inversion Pattern |
|----|----|----|----|---------------|----|----|----|----|-------------------|
| 0 | 0 | 0 | 0 | ABC | 0 | 0 | 0 | 0 | Normal Normal Normal |
| 0 | 0 | 0 | 1 | ACB | 0 | 0 | 0 | 1 | Normal Normal Invert |
| 0 | 0 | 1 | 0 | CBA | 0 | 0 | 1 | 0 | Normal Invert Normal |
| 0 | 1 | 0 | 0 | CAB | 0 | 1 | 0 | 0 | Normal Invert Invert |
| 0 | 1 | 0 | 1 | BAC | 0 | 1 | 0 | 1 | Invert Normal Normal |
| 0 | 1 | 1 | 0 | BCA | 0 | 1 | 1 | 0 | Invert Normal Invert |
| 1 | 0 | 0 | 0 | ACB | 1 | 0 | 0 | 0 | Invert Invert Normal |
| 1 | 0 | 0 | 1 | CAB | 1 | 0 | 0 | 1 | Invert Invert Invert |
| 1 | 0 | 1 | 0 | BCA | 1 | 0 | 1 | 0 | Invert Invert Invert |

METHOD AND APPARATUS TO FACILITATE TRANSMISSION OF AN ENCRYPTED ROLLING CODE

RELATED APPLICATIONS

This application is a continuation of U.S. application Ser. No. 13/777,787, filed Feb. 26, 2013; which is a continuation of U.S. application Ser. No. 11/501,455 filed Aug. 9, 2006, which issued as U.S. Pat. No. 8,422,667, on Apr. 16, 2013; which is a continuation in part of:
  U.S. application Ser. No. 11/480,288 filed on Jun. 30, 2006, which issued as U.S. Pat. No. 7,561,075, on Jul. 14, 2009, which is a continuation of U.S. application Ser. No. 11/044,411, filed on Jan. 27, 2005, issued as U.S. Pat. No. 7,071,850, on Jul. 4, 2006; and
  U.S. application Ser. No. 11/172,525, filed Jun. 30, 2005, which issued as U.S. Pat. No. 9,148,409, on Sep. 29, 2015;
the contents of each of which are fully incorporated herein by this reference.

TECHNICAL FIELD

This invention relates generally to encrypted rolling codes and more particularly to the transmission of encrypted rolling code information.

BACKGROUND

Rolling codes are known in the art. Rolling codes are often used, for example, in conjunction with movable barrier operators of various kinds (with movable barrier operators of various kinds also being known in the art and including operators that effect the selective control and movement of single panel and segmented garage doors, pivoting, rolling, and swinging gates, guard arms, rolling shutters, and various other movable barriers). In such an application setting, a wireless transmitter can send a code to a corresponding movable barrier operator to cause the latter to effect a desired movement or other action with respect to, for example, a corresponding movable barrier.

When using rolling codes, the code transmitted by the wireless transmitter will change (often with each transmission) in accordance with a predetermined plan or algorithm that is also known to the movable barrier operator. Such an approach can foil the use of an intercepted code by an unauthorized party because that intercepted code will not typically again, at least in the near term, be honored by that movable barrier operator should the unauthorized party attempt to themselves transmit that code. Without knowledge of the underlying scheme by which a next code is selected, the unauthorized party who gains access to a presently used code will still remain unable to leverage that knowledge in support of effecting unauthorized control over the movable barrier operator.

There may be instances, however, when additional security may be desired or appropriate. For example, a given rolling code instantiation may be open to brute force attacks or other weaknesses due to local and/or otherwise unique circumstances.

BRIEF DESCRIPTION OF THE DRAWINGS

The above needs are at least partially met through provision of the method and apparatus to facilitate transmission of an encrypted rolling code described in the following detailed description, particularly when studied in conjunction with the drawings, wherein:

FIG. 3 comprises a depiction of prior art ternary encoding;

FIG. 4 comprises a flow diagram as configured in accordance with various embodiments of the invention;

FIG. 5 comprises a flow diagram as configured in accordance with various embodiments of the invention;

FIG. 6 comprises a mapping table as configured in accordance with various embodiments of the invention;

FIG. 13 comprises a schematic view of a joint message as configured in accordance with various embodiments of the invention;

FIG. 14 comprises an illustrative example of a lookup table as configured in accordance with various embodiments of the invention;

Figure 1:
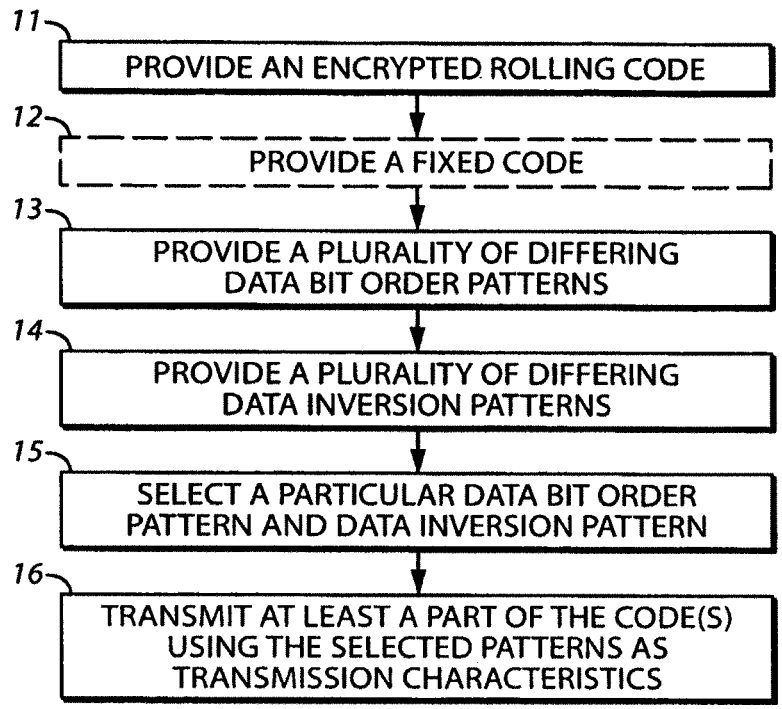
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will also be understood that the terms and expressions used herein have the ordinary meaning as is accorded to such terms and expressions with respect to their corresponding respective areas of inquiry and study except where specific meanings have otherwise been set forth herein.

DETAILED DESCRIPTION

Generally speaking, pursuant to these various embodiments, an encrypted rolling code, a plurality of differing data bit order patterns, and a plurality of differing data inversion patterns are provided. One selects a particular one of each of the bit order patterns and the data inversion patterns to provide selected patterns and then uses those selected patterns as transmission characteristics when transmitting at least part of the encrypted rolling code.

By these teachings, for example, a wireless remote control transmitter can be provided with data to be transmitted, where that data comprises, at least in part, at least portions of an encrypted rolling code and where that data comports with a particular data bit order pattern and a particular data inversion pattern as a function of a given portion of that rolling code. That data can then be transmitted in combination with the given portion of the encrypted rolling code wherein that given portion of the rolling code is not transmitted with any of its bits reordered or inverted as a function of the given portion itself. Accordingly, a receiver that receives the data can then properly recover the re-ordered/inverted portions of the encrypted rolling code as a function of the given portion of the encrypted rolling code.

By one approach, if desired, the aforementioned data can comprise ternary data that is presented in a binary format. The use of ternary data can aid in facilitating compatible interaction with at least some movable barrier operators while also achieving an encryption effect at the same time as tending to ensure compatible use with binary peripheral platforms and the like. By one approach, this can comprise mapping each trit of the ternary data to a corresponding pair of binary bits. A pair of binary bits can represent 4 discrete information elements and by one approach, three of these discrete information elements can each correspond to one of the three trit states/levels while the fourth discrete information element (which otherwise comprises an illegal value) can serve a synchronization function.

If desired, in addition to the aforementioned encrypted rolling code, a fixed code can also be included in the transmission. By one approach, for example, both the aforementioned part of the encrypted rolling code and this fixed code can be transmitted using the above-described selected patterns as transmission characteristics.

These and other benefits may become clearer upon making a thorough review and study of the following detailed description. Referring now to the drawings, and in particular to FIG. 1, an illustrative process in this regard provides 11 an encrypted rolling code. As will be illustrated in more detail below, this can comprise, if desired, providing an encrypted rolling code as a plurality of bit pairs as correspond to a ternary data set.

If desired, this process will also optionally accommodate providing 12 a fixed code. This fixed code can vary with the needs, requirements, and/or opportunities of a given application setting, but can, for example, comprise a value that is substantially unique to a given transmitter and hence comprises a value that will serve to identify that given transmitter. Such an approach can be useful, for example, when used in conjunction with a remote control movable barrier operator transmitter.

This process also provides 13 a plurality of differing data bit order patterns. By one approach, for example, this can comprise data bit order patterns that each comprise a pattern for exactly three bits. As will be shown below, this can be particularly beneficial when used in conjunction with bit pairs that correlate to corresponding ternary data. Similarly, this process provides 14 a plurality of different data inversion patterns. As before, if desired, this can comprise providing patterns that each comprise a pattern for exactly three bits. The number of patterns provided in either case can vary as desired. By one approach, however, this can comprise providing at least nine different bit order patterns and nine different data inversion patterns. Illustrative examples in this regard are provided further herein.

This process then provides for selecting 15 a particular one of each of the data bit order patterns and the data inversion patterns to provide resultant corresponding selected patterns. There are various ways by which such selections can be made. By one approach, one may use a predetermined portion of the previously provided encrypted rolling code to inform the making of these selections. For example (and as will be illustrated in more detail herein), this can comprise using a predetermined four bit pairs of the encrypted rolling code as a basis for selecting the particular data bit order pattern and the particular data inversion pattern. As another example in this regard, in combination with the foregoing or in lieu thereof, this can comprise using a first predetermined portion of the encrypted rolling code to select a first particular data bit order pattern and a first data inversion pattern and using a second predetermined portion of the encrypted rolling code (that is, for example, discrete with respect to the first predetermined portion of the encrypted rolling code though this is not a fundamental requirement) to select a second particular data bit order pattern and a second data inversion pattern.

This process then provides for transmitting 16 at least a part of the encrypted rolling code itself (as well as at least a part of the above-described fixed code when present) using the aforementioned selected patterns as transmission characteristics. By one approach this can comprise making such a transmission using Manchester encoding as is known in the art.

So configured, these teachings are readily employed, for example, to facilitate the transmission of a remote control message. This can comprise, for example, providing a fixed message having at least a first part and a second part along with an encrypted rolling code that has a first through a fourth part. The first part of the encrypted rolling code can then be used to select a particular data bit order pattern and a data inversion pattern to use as a set of first selected patterns while the second part of the encrypted rolling code can be used to select a second set of patterns from amongst the available candidate patterns. One can then transmit the first part of the fixed message and the third part of the encrypted rolling code using the first selected patterns as transmission characteristics while transmitting the second part of the fixed message and the fourth art of the encrypted rolling code using the second selected patterns as transmission characteristics.

By one approach, in this illustrative example this can also comprise transmitting the first and second parts of the encrypted rolling code without using either the first or selected patterns as transmission characteristics. So configured, the first and second parts of the encrypted rolling code are then readily usable as recovery identifiers that can be used by a receiver to recover the first and second parts of the fixed message and the third and fourth parts of the encrypted rolling code.

To illustrate further in this regard, these first and second parts of the encrypted rolling code could each comprise four bit pairs as correspond to the aforementioned ternary data. In such a case, two of the bit pairs as comprise the first part of the encrypted rolling code can be used with a lookup table to correlate those two bit pairs to a corresponding data bit order pattern. In a similar manner the remaining bit pairs can be used with a second lookup table (which may, if desired, actually comprise a part of the first lookup table) to correlate these bit pairs with a corresponding data inversion pattern. In a similar fashion, two of the bit pairs of the four bit pairs as comprise the second part of the encrypted rolling code can be used with that first lookup table to identify another data bit order pattern while the remaining two bit pairs can be used with the second lookup table to identify a corresponding data inversion pattern.

In such a case, the aforementioned transmission can then comprise transmitting the second part of the fixed message and the fourth part of the encrypted rolling code using the second selected patterns as transmission characteristics only after not transmitting for at least a predetermined period of time following transmission of the first part of the fixed message and the third part of the encrypted rolling code using the first selected patterns as transmission characteristics. The duration of this predetermined period of time can vary with the needs and opportunities of a given application setting, but a duration of about 75 milliseconds will suffice for many expected purposes.

In addition to facilitating a transmission of an encrypted rolling code and other content that comprises, for example, information that is unique to a given transmitter (such as a unique identifier for that transmitter), these teachings will further readily accommodate the transmission of additional data that is not substantially unique to the transmitter. This can comprise, for example, providing a data payload (such as a remote control instruction such as OPEN, CLOSE, VACATION MODE, LIGHTS ON, LIGHTS OFF, and so forth) that is not substantially unique to a given transmitter and then transmitting the first part of the fixed message, the third part of the encrypted rolling code, and a first part of this data payload while using the first selected patterns as transmission characteristics and transmitting the second part of the fixed message, the fourth part of the encrypted rolling code, and a second (remaining) portion of the data payload using the second selected patterns as transmission characteristics. When the data payload comprises a relatively large quantity of data as compared to the fixed message and/or the encrypted rolling code, additional portions of the data payload as are not accommodated by the just-described process can then be supplementally transmitted using one of the already selected patterns (or other patterns, if desired) as transmission characteristics.

Figure 2:
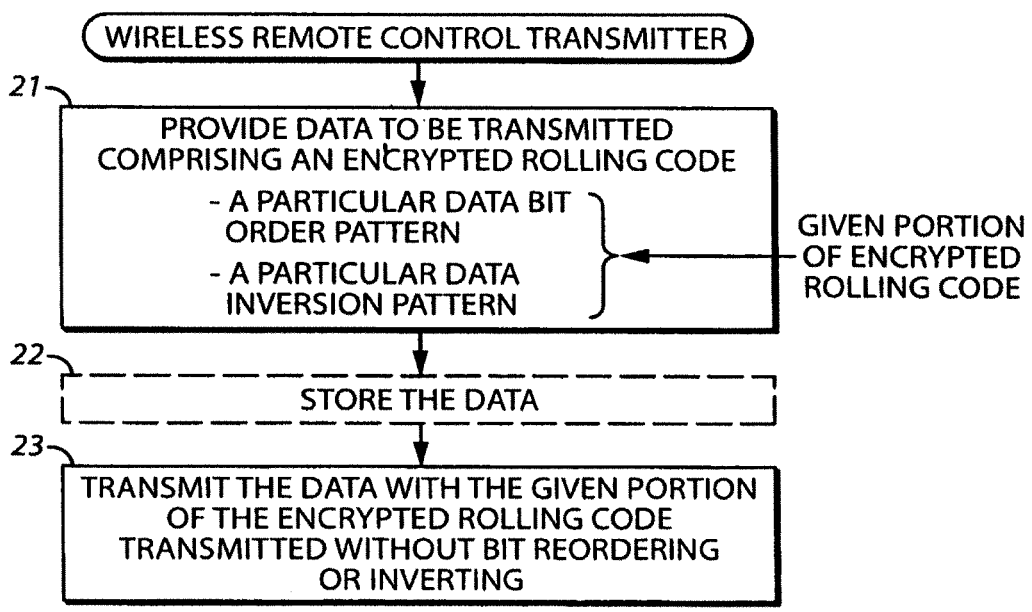
FIG. 2 comprises a flow diagram as configured in accordance with various embodiments of the invention.

As another specific illustrative example in this regard, and referring now to FIG. 2, a wireless remote control transmitter (such as a movable barrier operator remote control) can be configured and arranged to provide 21 data to be transmitted. This data can comprise, at least in part, at least portions of an encrypted rolling code. In any event, this data will comport with a particular data bit order pattern and a particular data inversion pattern as a function of a given portion of the rolling code. By one approach, if desired, this process can further comprise, at least in part, storing 22 this data in a memory prior to transmitting the data. The duration of such storage can vary considerably depending upon the specifics of a given application setting.

This wireless remote control transmitter can then transmit 23 this data in combination with the given portion of the encrypted rolling code such that the given portion of the encrypted rolling code is not transmitted with any of its bits reordered or inverted as a function of the given portion of the encrypted rolling code. So configured, a receiver that receives this data can properly recover the modified portions of the encrypted rolling code as a function, at least in part, of the unmodified given portion of the encrypted rolling code.

As noted above, these teachings are readily applied in a context that makes use of ternary data. It may therefore be helpful to first describe in more detail a typical ternary data protocol as one finds often deployed in conjunction with many movable barrier operators. Pursuant to one approach, pulses of similar amplitude have one of three different durations. For example, and referring now to FIG. 3, a first pulse 31, having a shortest duration, can represent the data element "0." A second pulse 32, having a medium length duration, can represent the data element or state "1." And a third pulse 33, having a longest duration, can represent the data element or state "2." Such a data mapping protocol serves well to effect a base three-based data exchange. The present teachings can accommodate use and leveraging of a ternary approach to effect relatively secure and compatible communications between a movable barrier operators and corresponding peripheral components of choice. These teachings are also compatible for use with an approach that eschews the specific ternary approach just described.

Referring now to FIG. 4, in general, these teachings will accommodate a process 40 that itself provides 41 ternary data as corresponds to a movable barrier operator and then converts 42 that ternary data to a binary format to provide resultant binary information. This binary information is then transmitted 43 from one platform to another. As will be shown below, this ternary-to-binary conversion process serves, at least in part, as a kind of encryption process which in turn aids in ensuring the authenticity and accuracy of the information being transmitted.

The ternary data itself can comprise, at least in part, bearer data. More particularly, and referring momentarily to FIG. 5, pursuant to one (optional) approach, provision of ternary data can comprise prior provision 51 of binary bits comprising information that corresponds to the movable barrier operator (for example, information sourced by, or intended for, a movable barrier operator). Such information can optionally comprise, for example, movable barrier operator fixed information 52 such as identifying information for a particular movable barrier operator, a particular peripheral component, or the like. Such information can also optionally comprise (in addition to or in lieu of fixed information 52) non-fixed information 53 such as the aforementioned data payload as again corresponds to the movable barrier operator. This non-fixed information 53 can comprise bearer data/information (such as, but not limited to, platform status information, commands, acknowledgments, and so forth). As already noted, this non-fixed information 53 can also comprise varying quantities of data if desired.

These binary bits are then converted 54 into the aforementioned ternary data. This could comprise, in an appropriate platform, a conversion of the binary data into ternary data such as that described above with respect to FIG. 3. In general, such an approach need not be used. Instead, the binary data can be converted into a binary-bit-based ternary format (with an illustrative example being provided further below).

By one approach, however, this does not comprise a simple reversal of the binary-to-ternary process just described. Instead, the ternary-to-binary conversion step can comprise mapping each trit of the ternary data to a corresponding pair of binary bits. To illustrate such a map 61, and referring momentarily to FIG. 6, the ternary data element "0" (which corresponds to the usual binary data element "0") maps to the binary pair "00." In similar fashion, ternary "1" (which corresponds to usual binary "1") maps to the binary pair "01" and ternary "2" (which corresponds to usual binary "11") maps to the binary pair "01."

This leaves an otherwise unused binary pair "11." Pursuant to a preferred approach, this otherwise illegal value can serve a synchronization function when facilitating communications as between a movable barrier operator and one or more peripheral components when using a binary format that otherwise has no synchronization mechanism built into its format (for example, a stream of binary bits such as:

0110111111010011101110110111111101001110111011011111110100111011111 which format lacks a frame marker or other point of synchronization). To illustrate, a synchronization signal/marker comprising this "11" binary pair can be used to indicate, for example, the regular end and/or start of a frame or message as in the following example:

11011011111101111011101111011011111110111111011111101101111111011111 where the bold font "11" regularly spaced binary pairs serve as frame markers (and which, due to their synchronized regular spacing, are readily distinguishable from other "11" pairs as may occur for whatever reason (illustratively depicted in the above example with italic font).

Those skilled in the art will appreciate that this process of converting binary information into ternary information, followed by conversion of that ternary information into corresponding binary pairs, yields, in most cases, a different bit sequence (and even a different number of bits) as compared to the initial binary information. This difference serves, at least in part, as a non-key-based encryption technique and hence provides a way of effecting the provision of an encrypted rolling code.

Figure 7:
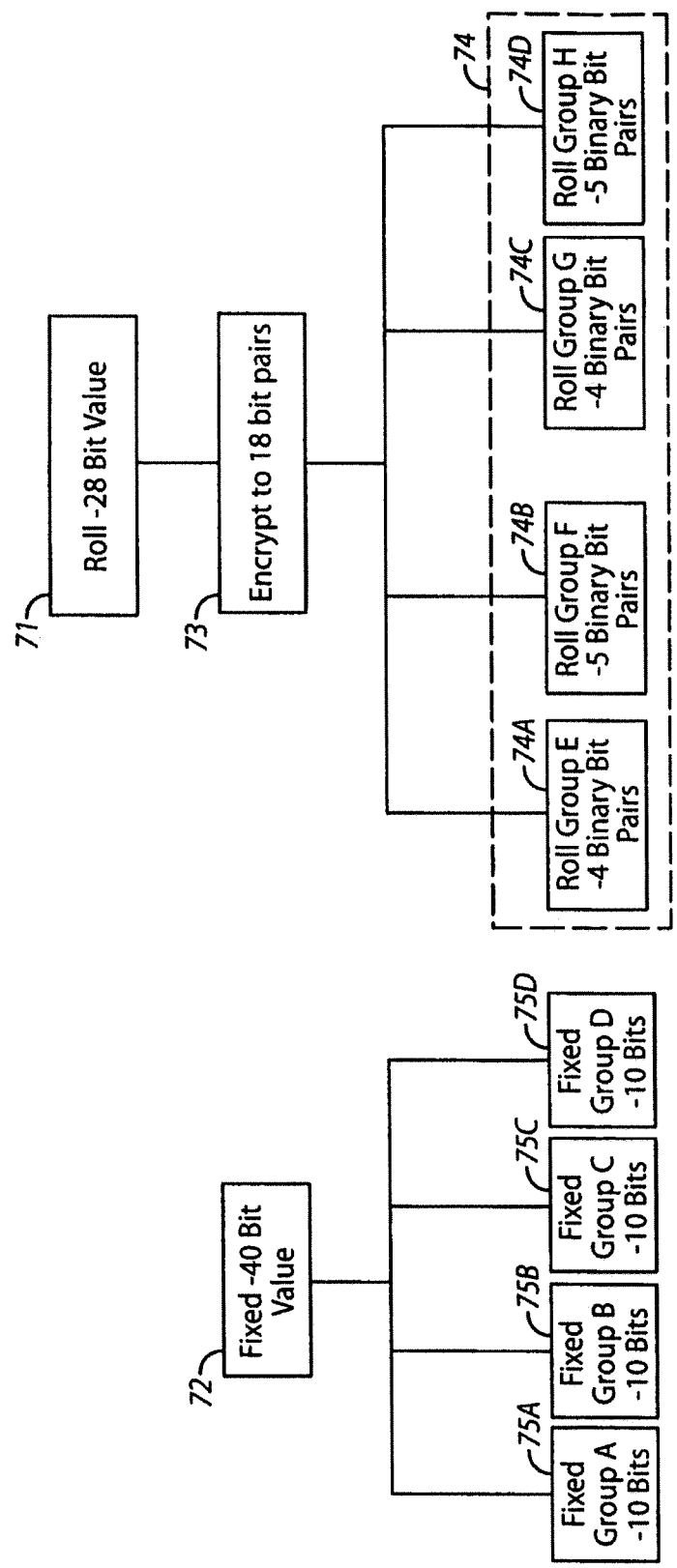
FIG. 7 comprises a schematic view of bit processing and parsing in accordance with various embodiments of the invention.

Referring now to FIG. 7, a more detailed illustrative embodiment will be presented. In this first illustrative example, the only substantive content to be associated and transmitted with a 28 bit rolling code 71 comprises a 40 bit value that represents fixed information 72. This fixed information 72 may serve, for example, to uniquely identify the transmitter that will ultimately transmit this information as noted above.

In this particular illustrative embodiment, the bits comprising the rolling code 71 are encrypted 73 by mirroring the bits and then translating those mirrored bits into ternary values as suggested above to provide corresponding bit pairs (in this example, this would comprise 18 such bit pairs) to thereby provide a resultant encrypted rolling code 74. This mirroring can be applied to specific groupings of bits in the rolling code creating mirrored groups or can involve the entire value. In this illustrative example, the encrypted rolling code 74 is presented for further processing as four groups. In this example, these four groups comprise a roll group E 74A comprised of four binary bit pairs, a roll group F 74B comprised of five binary bit pairs, a roll group G 74C comprised of four binary bit pairs, and a roll group H 74D comprised of five binary bit pairs.

The 40 bit fixed information 72 is subdivided in a similar manner albeit sans encryption. This comprises, in this particular illustrative approach, forming four subgroups comprising a fixed group A 75A, a fixed group B 75B, a fixed group C 75C, and a fixed group D 75D, wherein each such group is comprised of 10 bits of the original 40 bit value.

Figure 8:
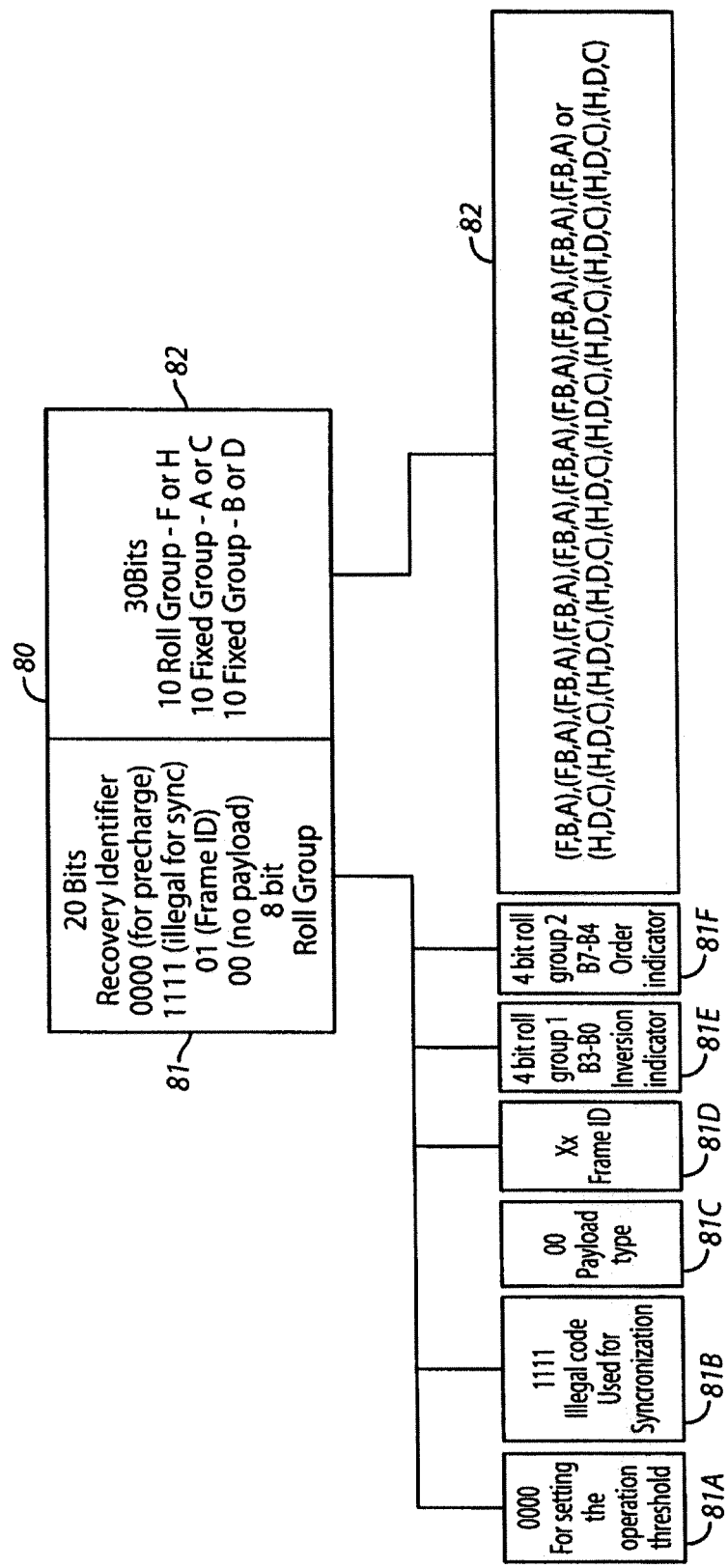
FIG. 8 comprises a comprises a schematic joint message diagram as configured in accordance with various embodiments of the invention.

These variously partitioned data groups can then be used as shown in FIG. 8 to effect a desired transmission. In this example, one or more joint messages 80 provide a primary vehicle by which to communicate the desired information (which includes both the encrypted rolling code and fixed information data as modified as a function of a given portion of the encrypted rolling code along with a recovery identifier that represents that given portion of the encrypted rolling code). This joint message 80 comprises, generally speaking, a first 20 bit portion 81 and a second 30 bit portion 82.

The first portion 81 comprises, in this embodiment, the following fields:

"0000"— these bits 81A serve to precharge the decoding process and effectively establish an operational threshold;

"1111"— these bits 81B comprise two bit pairs that present the illegal state "11" ("illegal" because this corresponds to a fourth unassigned state in the ternary context of these communications) and serve here as a basis for facilitating synchronization with a receiving platform;

"00"— this bit pair 81C identifies a type of payload being borne by the joint message (in this embodiment, "00" corresponds to no payload other than the fixed identifying information for the transmitter itself, "01" corresponds to a supplemental data payload, and "10" corresponds to a supplemental data-only payload— further explanation regarding these payload types appears further below);

"Xx"—this bit pair 81D presents a frame identifier that can be used by a receiver to determine whether all required joint messages 80 have been received and which can also be used to facilitate proper reconstruction of the transmitted data;

"B3, B2, B1, B0"— these two bit pairs 81E comprise an inversion pattern recovery identifier and are selected from the bits that comprise the encrypted rolling code 74 described above;

"B7, B6, B5, B4"— these two bit pairs 81F comprise a bit order pattern recovery identifier and are also selected from the bits that comprise the encrypted rolling code 74 described above.

Figures 9, 10:
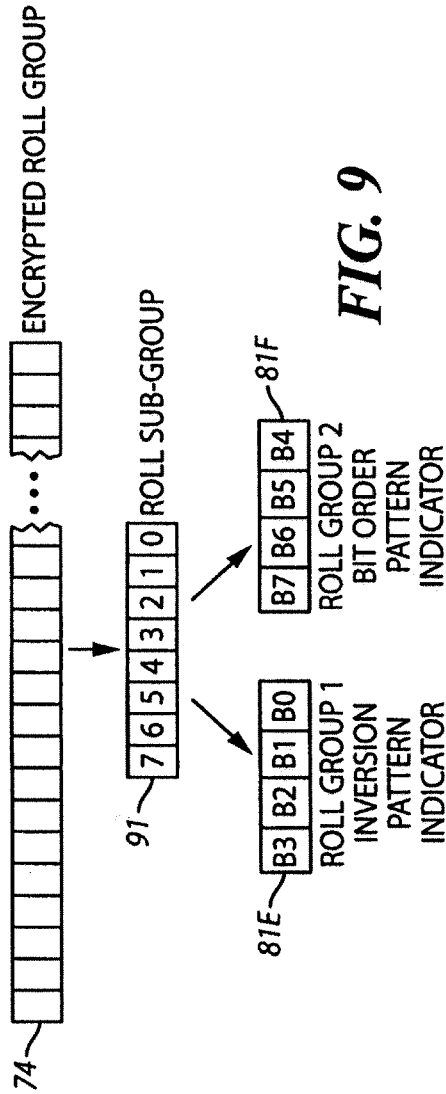
FIG. 9 comprises a schematic view of bit selection and parsing as configured in accordance with various embodiments of the invention.
FIG. 10 comprises an illustrative example of a lookup table as configured in accordance with various embodiments of the invention.

There are various ways by which these recover identifier values can be selected. Referring momentarily to FIG. 9, by one approach, eight bits from the encrypted roll group 74 are selected to form a corresponding roll sub-group 91. These might comprise, for example, the first or the last eight bits of the encrypted roll group 74 (in a forward or reversed order). These might also comprise, for example, any eight consecutive bits beginning with any pre-selected bit position (such as, to illustrate, the seventh bit, the 21$^{st}$ bit, and so forth). Other possibilities also exist. For example, only even position bits or odd position bits could serve in this regard. It would also be possible, for example, to use preselected bits as comprise one or more of the previously described roll group sub-groups such as roll group E 74A or roll group G 74C.

It would also be possible to vary the selection mechanism from, for example, joint message to joint message. By one simple approach in this regard, for example, the first eight bits of the encrypted roll group 74 could be used to form the roll sub-group 91 with the last eight bits of the encrypted roll group 74 being used in a similar fashion in an alternating manner.

The eight bits that comprise this roll sub-group 91 are then further parsed to form the two recovery indicators 81E and 81F mentioned above. Again, there are numerous ways by which one may use the bits that comprise the roll sub-group 91 to form these recovery indicators 81E and 81F. By one simple approach, for example, the bits as comprise the roll sub-group 91 can be used in their existing (or reversed) order to form roll group 1 81E and roll group 2 81F. Using this approach, for example, bit B3 of roll group 1 81E would comprise bit seven from the roll sub-group 91 with bit B2 then corresponding to bit six and so forth.

By another approach, if desired, every other bit can be applied in this manner. So configured, for example, bit B3 could comprise bit six from the roll sub-group 91, bit B2 could comprise bit four from the roll sub-group 91, and so forth. In such a case, bit B7 would then comprise bit seven from the roll sub-group 91, bit B6 would comprise bit five from the roll sub-group 91, and so forth.

Referring again to FIG. 8, in this embodiment, the "B7, B6, B5, B4" values from the corresponding recovery indicator are used in conjunction with one or more lookup tables to determine a data bit order pattern to use with respect to formatting the data as comprises the second portion 82 of the joint message 80. Similarly, the "B3, B2, B1, B0" values are used in conjunction with a lookup table to determine a data bit order pattern to also use with that second portion 82 of the joint message 80.

Before providing further elaboration regarding an illustrative example of such lookup tables and their use, it will be helpful to first note that, in this example, the data in the second portion 82 of the joint message comprises 10 bits from roll group F (or H) and 10 bits each from fixed group A (or C) and fixed group B (or D) for a total of 30 bits. These bits are organized into triplets (shown in FIG. 8 in the form "(F, B, A)" and "(H, D, C)" to indicate that each such triplet includes one bit from a roll group F or H and one bit each from the two fixed groups B and A or D and C.

Those skilled in the art will note that, in this illustrative example, bits from roll group E 74A and roll group G 74C are not present in the second portion 82 of the joint message 80. This is because, in this example, it is presumed that the contents of these two roll groups are used to form the recovery indicators that appear in the first portion 81 of the joint message 80. Other accommodations can of course be made in this regard. In general, however, these teachings will accommodate not including those encrypted rolling code bits that are used as recovery indicators in the second portion 82 of the joint message 80.

In the example shown, the order of the bits in each triplet is "F, B, A" (or "H, D, C" as appropriate). This order is neither arbitrary nor static. Instead, for this particular joint message 80, this order of the bits in each triplet is dictated by the values B7, B6, B5, B4 noted above. In this case, and referring now to FIG. 10, a lookup table 101 serves to correlate various values for these two bit pairs with corresponding data bit order patterns. In this example, presuming that the values of these four bits happens to be "0000," the corresponding order of bits for each triplet is established as "F/H, B/D, A/C" and hence the ordering of the bits depicted in FIG. 8.

Those skilled in the art will note that this lookup table 101 provides no patterns that would correlate to two bit pairs having the value "11." This is because, in this embodiment, "11" as a bit pair value comprises an illegal value and hence is not expected to occur. Accordingly there are no bit order patterns presented to correlate with such values as "11XX," "XXII," or "1111." This creates 9 possible selections for the order of bits and the inversion value. The number of possible unique order of three bits leads to only six different bit order patterns. This degree of diversity should suffice for most if not all purposes.

The aforementioned B3, B2, B1, B0 values 81F are employed in a similar fashion with this lookup table 101 to identify a particular inversion pattern to be employed with the data triplets of the second portion 82 of the joint message 80. For example, when these bits are "0000," this lookup table provides for no inversion of any of the bits in each triplet. On the other hand, when these bits are "1010," each bit of each triplet is to be inverted. In this case, up to eight different inversion patterns are possible.

To illustrate further, when a given data triplet happens to have the values "110" and the inversion indicator has the values "0100," the lookup table will return a data inversion pattern of "normal invert invert." As a result, this particular data triplet will instead have the values "101" because the second and third values in each triplet are now to be inverted in value.

So configured, a first portion of a joint message is seen to include a recovery indicator that itself comprises a selected portion of an encrypted rolling code. A second portion of that joint message, in turn, contains data triplets having bits that are arranged in a particular order and that observe a particular inversion pattern as a function of that joint indicator. Accordingly, it will not be sufficient for an unauthorized party to simply glean, in some fashion, the basis of the rolling code itself. Instead, now, this unauthorized party must also now understand how a particular portion of that rolling code is used to modify the transmission of other portions of that rolling code in addition to fixed information as may also accompany the rolling code.

Figure 11:
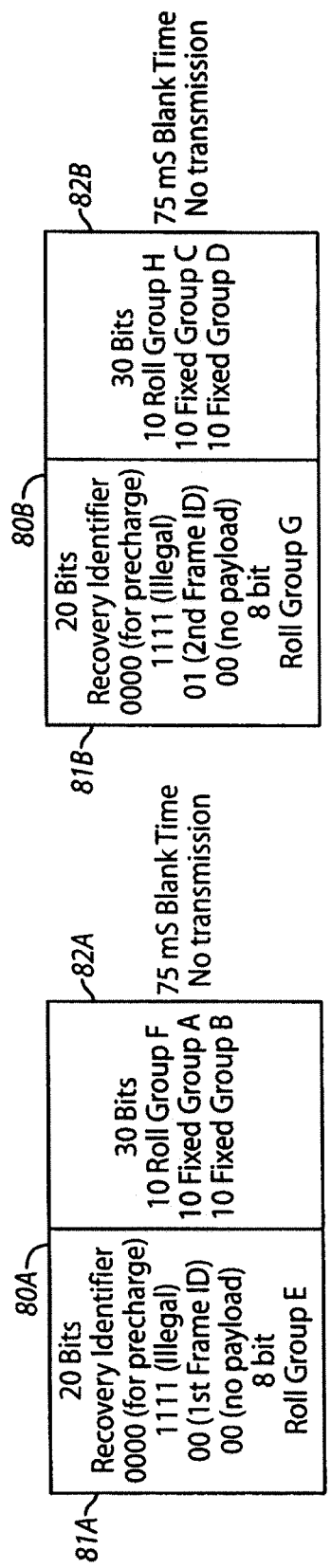
FIG. 11 comprises a schematic view of two joint messages as configured in accordance with various embodiments of the invention.

In many application settings it may be desirable to present more than one such joint message to present a complete transmission. For example, and referring now to FIG. 11, it may be desirable to use two (or more) such joint messages 80A and 80B in order to present the complete rolling code and the complete fixed content and was described above. In such a case, for example, the first joint message 80A can present and use a first roll sub-group 91 as defined above as a recovery identifier (which comprises, in this illustrative example, roll group E 74A) while the second joint message 80B presents and uses a second, different roll sub-group B 91 (which comprises, in this illustrative example, roll group G 74C) for this purpose. These recovery identifiers can be used as just described to control modification of their corresponding data. So configured, in this illustrative example, 10 bits of roll group F 74B, 10 bits of fixed group A 75A, and 10 bits of fixed group B 75B have their bits ordered and inverted as a function of the bits of roll group E 74A while 10 bits of roll group H 74D, 10 bits of fixed group C 75C, and 10 bits of fixed group D 75D are similarly ordered/inverted as a function of the bits of roll group G 74C.

If desired, these joint messages 80A and 80B can be sent in a concatenated manner. By another approach, however, these joint messages can be separated by at least a minimal amount of silence (achieved, for example, by not transmitting during this period of time). For example, 75 milliseconds or so of blank time can be used for this purpose. So configured, a receiver that receives a second joint message prior to this period of blank time expiring can conclude that one or both of the received messages is somehow in error and should be avoided.

Figure 12:
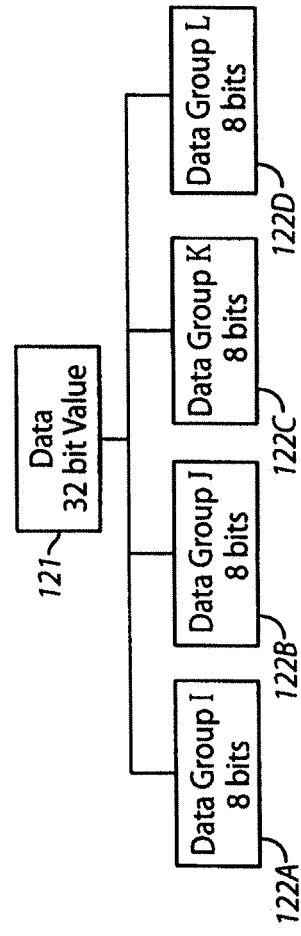
FIG. 12 comprises a schematic view of bit parsing as configured in accordance with various embodiments of the invention.

As noted above, in some cases it may be useful to transmit an additional amount of data or information than that specifically provided above. For example, it may be useful to transmit additional data that represents a particular instruction, status information, or the like. Such additional information can be readily accommodated by the teachings set forth above. To illustrate, and referring now to FIG. 12, 32 bits of such additional data can be subdivided into four corresponding data groups I and J 122A and 122B and K and L 122C and 122D where each such data group has eight bits.

Referring now to FIG. 13, the second portion 82 of each joint message 80 can now comprise 54 bits. By one approach, this can comprise 8 bits for a repeated presentation of the same rolling code group E or G as comprises the recovery identifier, 10 bits each for rolling code group F or H, fixed group A or C, and fixed group B or D, as well as 8 bits each for data group I or K and data group J or L as are described above. These various bits are again combined into data triplets using a group selection pattern such as that illustrated in FIG. 13. And, once again, the recovery identifier comprised of the roll group presented in the first portion 81 of the joint message 80 is used to select from a lookup table(s) the particular bit order and inversion patterns to employ with respect to these data triplets. In this case, and referring now to FIG. 14, the lookup table 141 can include specific bit order patterns that apply in different ways depending upon whether the data triplet includes the supplemental data.

Figure 15:
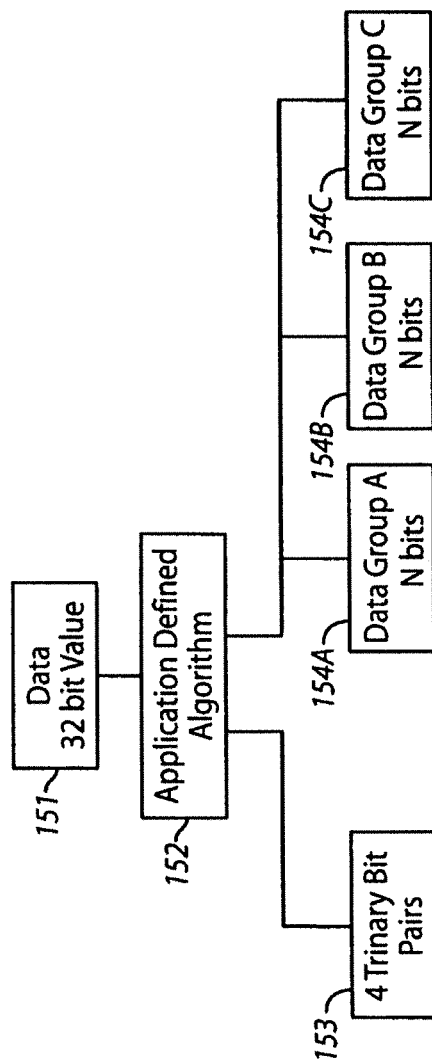
FIG. 15 comprises a schematic view of bit processing and parsing as configured in accordance with various embodiments of the invention.

In some cases, it may be necessary or appropriate to transmit even a larger quantity of data than can be accommodated by the processes and techniques described above. In such a case, if desired, additional supplemental joint messages can be used to present such supplemental data. With reference to FIG. 15, 32 bit value data elements 151 can be parsed using an application defined algorithm 152 of choice as corresponds to the data itself (or as may be otherwise provided or selected) into four ternary bit pairs 153 and three data groups of N bits each 154A-154C.

Figure 16:
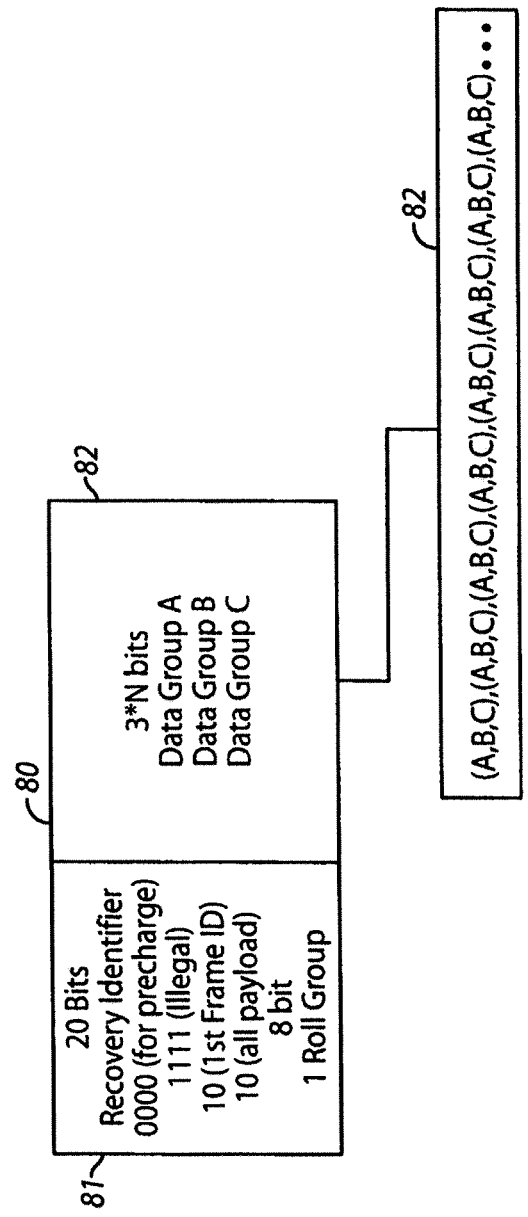
FIG. 16 comprises a schematic view of a joint message as configured in accordance with various embodiments of the invention.

Referring now to FIG. 16, the recovery indicator can be reused from a previous related joint message and the second portion 82 of the joint message 80 can contain 3 to the Nth power bits as necessary to accommodate the full data payload. The three data groups A-C are then used to form corresponding data triplets. And, as before, the recovery identifier is used to extract from a corresponding lookup table (such as the lookup table 171 presented in FIG. 17) the particular bit order pattern and bit inversion pattern to employ with respect to the transmission of these data triplets.

Figures 17, 18:
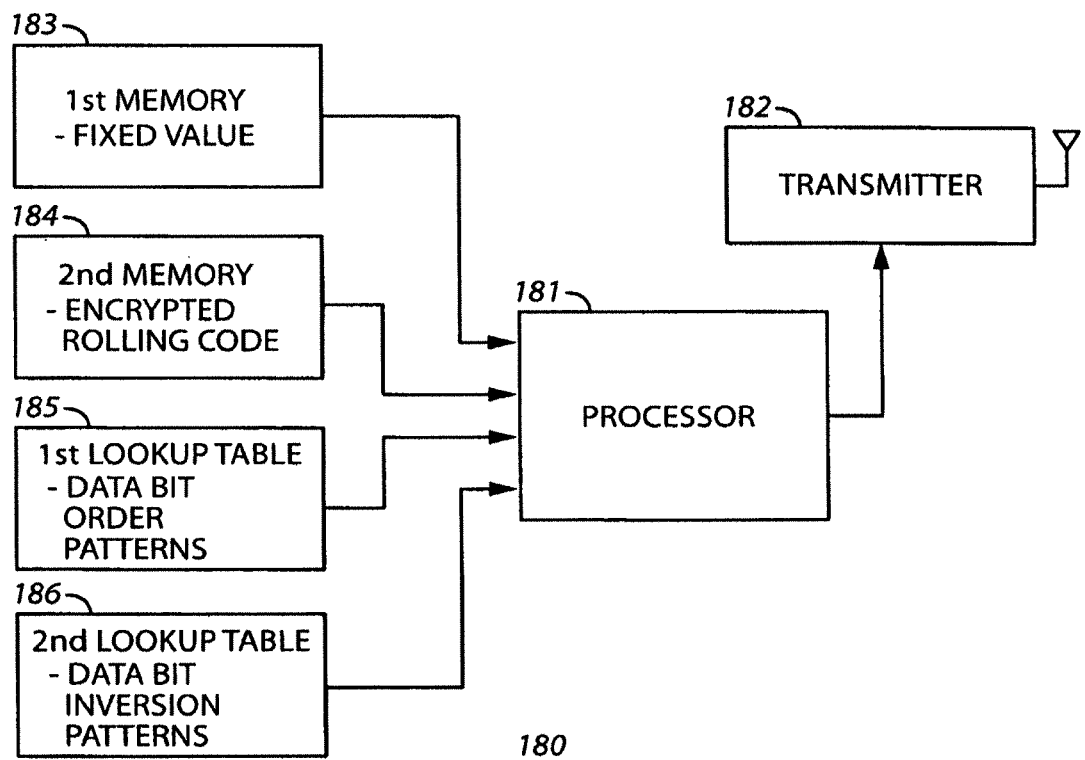
FIG. 17 comprises an illustrative example of a lookup table as configured in accordance with various embodiments of the invention.
FIG. 18 comprises a block diagram as configured in accordance with various embodiments of the invention.

Those skilled in the art will appreciate that the above-described processes are readily enabled using any of a wide variety of available and/or readily configured platforms, including partially or wholly programmable platforms as are known in the art or dedicated purpose platforms as may be desired for some applications. Referring now to FIG. 18, an illustrative approach to such a platform will now be provided.

In this illustrative embodiment, the apparatus 180 (which may comprise, for example, a wireless remote control transmitter) comprises a processor 181 that couples to a transmitter 182 (such as a wireless transmitter) of choice. Both of these components then also operably couple to a first memory 183, a second memory 184, a first lookup table 185, and a second lookup table 186. The first memory 183 can have a fixed value stored therein. This fixed value can comprise, for example, information that substantially uniquely identifies this particular apparatus 180. This first memory 183 may also, if desired, have a plurality of different fixed values contained therein. This would permit storing, for example, remote control signals that are not specific (i.e., unique) to the apparatus 180 itself.

The second memory 184 can have the aforementioned encrypted rolling code stored therein. By one approach, the processor 181 is configured and arranged to calculate the encrypted rolling code when needed and to temporarily buffer that value in the second memory 184 pending actual use of that information. By another approach, the encrypted rolling code information can be pre-provisioned using a derivation and storage approach of choice.

The lookup tables 185 and 186 are the lookup tables described above. For example, the first lookup table 185 can comprise the lookup table that correlates a first plurality of different encrypted rolling code values with corresponding differing data bit order patterns. Similarly, the second lookup table 186 can comprise the lookup table that correlates a second plurality of different encrypted rolling code values with corresponding different data inversion patterns.

The processor 181 itself is configured and arranged (via, for example, appropriate programming) to carry out selected teachings as have been presented above. So configured, for example, the processor 181 can be configured and arranged to use the encrypted rolling code to select ones of the particular data bit order patterns and data inversion patterns for the transmitter 182 to use as transmission characteristics when transmitting the fixed value and at least portions of the encrypted rolling code. In particular, if desired, the processor can use a first part of the encrypted rolling code to select a data bit order pattern and a data inversion pattern to use when transmitting a first part of the encrypted rolling code and the fixed value and a second, different part of the encrypted rolling code to select a data bit order pattern and a data inversion pattern to use when transmitting a second, different part of the encrypted rolling code and the fixed value.

Those skilled in the art will recognize and understand that such an apparatus 180 may be comprised of a plurality of physically distinct elements as is suggested by the illustration shown in FIG. 18. It is also possible, however, to view this illustration as comprising a logical view, in which case one or more of these elements can be enabled and realized via a shared platform and/or a more-widely-distributed platform. It will also be understood that such a shared platform may comprise a wholly or at least partially programmable platform as are known in the art.

So configured, those skilled in the art will recognize and appreciate that these teachings offer great flexibility and opportunity with respect to further protecting information during a wireless transmission of that information. These teachings have particular relevance to transmissions of rolling codes and offer particular advantages when also used in conjunction with the transmission of fixed information in addition to rolling code information. The particular transmission characteristics presented are largely compatible for use with a wide variety of wireless modulation techniques. Those skilled in the art will also appreciate that these teachings are highly compatible for use with binary-based representations of ternary data formats.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

What is claimed is:

1. An apparatus comprising:
a processor configured to use a rolling code to:
select a particular data bit order pattern from a plurality of potential data hit order patterns; and
select a particular data inversion pattern from a plurality of potential data inversion patterns;
the processor further configured to provide a message comprising (i) at least a part of the rolling code and a fixed code; and
a transmitter operably coupled to the processor and configured to transmit the message using the particular data hit order pattern and the particular data inversion pattern as transmission characteristics.

2. The apparatus of claim 1. wherein the apparatus comprises a wireless remote control transmitter.

3. The apparatus claim 2, wherein the wireless remote control transmitter is configured to communicate the message; and
wherein the message is received by a movable barrier operator.

4. The apparatus of claim 3, wherein the message received by the movable barrier operator effects an action by the movable harrier operator.

5. The apparatus of claim 1. wherein the fixed code comprises a first fixed code part and a second fixed code part and the rolling code comprises a first rolling code part, a second rolling code part, a third rolling code part, and a fourth rolling code part, and wherein the processor is further configured to:
use the first rolling code part to select the particular data bit order pattern and the particular data inversion pattern to use for transmission of the third rolling code part and the first fixed code part; and
use the second rolling code part to select a second data hit order pattern and a second data inversion pattern to use for transmission of the fourth rolling code part and the second fixed code part.

6. The apparatus of claim 1, wherein the fixed code comprises a substantially unique identifier for the apparatus.

7. The apparatus of claim 5, wherein the fixed code comprises both a substantially unique identifier for the apparatus and a remote control signal that is not specific to the apparatus.

8. The apparatus of claim 1, wherein the rolling code is an encrypted rolling code.

9. The apparatus of claim 5, wherein the processor is further configured to;
use the first rolling code part and a first lookup table to select the particular data bit order pattern; and
use the second rolling code part and a second lookup table to select the second data inversion pattern.

10. The apparatus of claim 1. wherein the apparatus comprises a wireless remote control transmitter configured to communicate the message with a garage door opener, and
wherein the message is configured to cause the garage door opener to change a position of a garage door associated with the garage door opener.

11. The apparatus of claim 1, wherein the rolling code is an encrypted rolling code; and
wherein the processor is configured to:
provide ternary data as corresponds to a movable barrier operator; and
convert the ternary data to a binary format to provide binary information as at least a part of the encrypted rolling code.

12. An apparatus composing:
a receiver configured to receive a message from a transmitter; and
a processor operably coupled to the receiver, the processor configured to recover, from the message, at least a portion of a rolling code, the message comprising a part thereof that was transmitted using a plurality of selected patterns of transmission characteristics selected based at least in part on the rolling code, wherein a first one of the plurality of selected patterns of transmission characteristics comprises a selected particular one of a plurality of differing data hit order patterns, and wherein a second one of the plurality of selected patterns of transmission characteristics comprises a selected particular one of a plurality of differing data inversion patterns.

13. The apparatus of claim 12, wherein the message further comprises, at least in part, a representation of the plurality of selected patterns of transmission characteristics.

14. The apparatus of claim 12, wherein the rolling code is an encrypted rolling code and wherein the message further comprises a fixed value.

15. The apparatus of claim 12, wherein the message further comprises:
a fixed portion including a first, fixed part and a second fixed part;
and wherein the rolling code includes a first rolling code part, a second rolling code part, a third rolling code part, and a fourth rolling code part;
wherein the first rolling code part was used by the transmitter to select a particular one of each of the plurality of differing data bit order patterns and the plurality of differing data inversion patterns to provide first selected patterns;
wherein the second rolling code part was used by the transmitter to select a particular one of each of the plurality of differing data bit order patterns and the plurality of differing data inversion patterns to provide second selected patterns: and
wherein the apparatus is further configured to use the first rolling code part and the second rolling code part as recovery identifiers to recover the first fixed part and the second fixed part and the third rolling code part and fourth rolling code part.

16. The apparatus of claim 15, wherein the transmitter is a wireless remote control transmitter and wherein the apparatus is a movable barrier operator.

17. The apparatus of claim 16, wherein the message is transmitted from the wireless remote control transmitter and received by the movable barrier operator to effect an action by the movable barrier operator to change a position of a moveable barrier.

18. A non-transitory computer readable medium comprising instructions which, when executed by a processor of an apparatus, cause the processor to perform operations comprising:
selecting, using a rolling code, a particular data bit order pattern from a plurality of potential data bit order patterns;
selecting, using the rolling code, a particular data inversion pattern from a plurality of potential data inversion patterns; providing a message comprising (i) at least a pan of the rolling code and (ii) a fixed code; and
causing the particular data bit order pattern and the particular data inversion pattern to be used as transmission characteristics for transmitting the message.

19. The non-transitory computer readable medium of claim 18, wherein the fixed code comprises a first fixed code part and a second fixed code part and the rolling code comprises a first rolling code part, a second rolling code part, a third rolling code part, and a fourth rolling code part, and wherein the operations further comprise:
using the first rolling code part to select the particular data bit order pattern and the particular data inversion pattern to use for transmission of the third rolling code part of the rolling code and the first fixed code part; and
using the second rolling code part to select a second data bit order pattern and a second data inversion pattern to use for transmission of the fourth rolling code part and the second fixed code part.

20. The non-transitory computer readable medium of claim 18, wherein the fixed code comprises a substantially unique identifier for the apparatus.

21. The non-transitory computer readable medium of claim 18, wherein the message is provided to a movable barrier operator to effect an action by the movable barrier operator to change a position of a moveable barrier.

\* \* \* \* \*